(12) United States Patent
Jakob et al.

(10) Patent No.: US 9,237,987 B2
(45) Date of Patent: Jan. 19, 2016

(54) METERING DEVICE

(75) Inventors: Thomas Jakob, Selb (DE); Frank Skaper, Leupoldsgrün (DE); Thorsten Kellner, Bayreuth (DE); Frank Richter, Harra (DE)

(73) Assignee: RAUMEDIC AG, Münchberg (DE)

( * ) Notice: Subject to any disclaimer, the term of this patent is extended or adjusted under 35 U.S.C. 154(b) by 177 days.

(21) Appl. No.: 13/988,474

(22) PCT Filed: Nov. 11, 2011

(86) PCT No.: PCT/EP2011/069956
§ 371 (c)(1),
(2), (4) Date: May 20, 2013

(87) PCT Pub. No.: WO2012/065921
PCT Pub. Date: May 24, 2012

(65) Prior Publication Data
US 2013/0253464 A1   Sep. 26, 2013

(30) Foreign Application Priority Data

Nov. 18, 2010  (DE) .......................... 10 2010 044 141

(51) Int. Cl.
*A61J 1/00* (2006.01)
*A61J 7/00* (2006.01)
(Continued)

(52) U.S. Cl.
CPC ................ *A61J 7/0076* (2013.01); *A45D 34/04* (2013.01); *A61J 7/0053* (2013.01); *A61M 5/19* (2013.01);
(Continued)

(58) Field of Classification Search
CPC .................. A61J 7/0053; A61J 7/0076; A61J 2001/2031; A61J 7/0015; A61M 5/178; A61M 2005/1787; A61M 5/19; A61M 2005/3123; A61M 2005/3125; A61M 2005/3126; A61M 2005/3128; A61M 5/3129; A61M 2005/3132; A61M 5/3135; A61M 5/315; A61M 5/31501; A61M 5/31505; A61M 5/31511; A61M 5/31533; A61M 5/31536; A61M 5/31593; A61M 5/31596; A61M 2005/31598; A61M 35/003; A45D 34/04; A45D 2200/054; A45D 2200/055; B05C 17/01; B05C 17/00; B05C 17/005; B05C 17/00553; B05C 17/00559; B05C 17/00563; B05C 17/00569; B05C 17/00573; B05C 17/00576; B05C 17/0116; B05C 17/015; A47G 21/183; G01F 11/027; G01F 11/025

See application file for complete search history.

(56) References Cited

U.S. PATENT DOCUMENTS 3,570,486 A * 3/1971 Engelsher et al. ............... 604/88
3,661,265 A * 5/1972 Greenspan .................... 210/359

(Continued)

FOREIGN PATENT DOCUMENTS

| DE | 3016772 C2 | 11/1980 |
| GB | 2121290 A | 12/1983 |
| WO | 2008122438 A2 | 10/2008 |
| WO | 2010043317 A1 | 4/2010 |
| WO | WO2010043317 * | 4/2010 |
| WO | 2010122981 A1 | 10/2010 |

*Primary Examiner* — Adam Marcetich
(74) *Attorney, Agent, or Firm* — Browdy and Neimark, PLLC

(57) ABSTRACT

A metering device is used for the metered administration of a flowable preparation together with a flowable carrier medium. A storage container for the preparation has at least one access opening. A metering plunger body can be moved in a sealed manner in the storage container between a starting position and at least one metering position. The metering plunger body is hollow. A metering sleeve has on a bottom side an eccentric metering sleeve opening. An inner plunger body has on the bottom side an eccentrically arranged plunger body opening. In a through relative rotation position of the metering sleeve relative to the inner plunger body a passage is provided between the inside of the storage container and the inside of the inner plunger body. In a closed relative rotational position this passage is closed. This results in a user-friendly and compact metering device.

21 Claims, 22 Drawing Sheets

(51) Int. Cl.
*A61M 5/19* (2006.01)
*A45D 34/04* (2006.01)
*A61M 5/315* (2006.01)
*A45D 40/20* (2006.01)
*A61M 5/31* (2006.01)
*B65D 81/32* (2006.01)

(52) U.S. Cl.
CPC ...... *A61M 5/31596* (2013.01); *A45D 2040/207* (2013.01); *A45D 2040/208* (2013.01); *A45D 2200/054* (2013.01); *A45D 2200/055* (2013.01); *A61J 1/2031* (2013.01); *A61M 2005/3125* (2013.01); *A61M 2005/3126* (2013.01); *A61M 2005/3128* (2013.01); *A61M 2005/31598* (2013.01); *B65D 81/325* (2013.01); *B65D 81/3255* (2013.01)

(56) References Cited

U.S. PATENT DOCUMENTS

| | | | | |
|---|---|---|---|---|
| 4,188,949 | A * | 2/1980 | Antoshkiw | 604/191 |
| 2004/0122359 | A1* | 6/2004 | Wenz et al. | 604/82 |
| 2005/0171506 | A1* | 8/2005 | Hallahan et al. | 604/514 |
| 2005/0177100 | A1* | 8/2005 | Harper et al. | 604/89 |
| 2005/0247741 | A1* | 11/2005 | Dieudonat | 222/405 |
| 2007/0017890 | A1 | 1/2007 | Al-Jadh | |
| 2009/0266843 | A1* | 10/2009 | Griesbaum et al. | 222/137 |
| 2010/0063473 | A1* | 3/2010 | Schwarz et al. | 604/514 |
| 2011/0005945 | A1* | 1/2011 | Nakatsuka et al. | B65D 81/3211 206/219 |
| 2012/0016319 | A1* | 1/2012 | Zino Gutierrez | 604/289 |
| 2012/0053529 | A1* | 3/2012 | Imai | 604/212 |

\* cited by examiner

METERING DEVICE

CROSS-REFERENCES TO RELATED APPLICATIONS

This application claims the priority of German Patent Application, Serial No. 10 2010 044 141.4, filed Nov. 18, 2010, pursuant to 35 U.S.C. 119(a)-(d), the content of which is incorporated herein by reference in its entirety as if fully set forth herein.

FIELD OF THE INVENTION

The invention relates to a metering device for the metered administration of a flowable preparation together with a flowable carrier medium.

BACKGROUND OF THE INVENTION

Such a metering device is known from WO 2010/043 317 A1. A further metering device is known from WO 2008/122 438 A2. A syringe for taking samples is known from DE 30 16 772 C2.

SUMMARY OF THE INVENTION

An objective of the present invention is to configure a metering device of the aforementioned kind to be user friendly and as compact as possible.

This objective is achieved according to the invention by a metering device for the metered administration of a flowable preparation together with a flowable carrier medium,
  with a storage container for the preparation, which communicates with the environment via at least one access opening,
  with a metering plunger body, which is displaceable in a sealed manner at least in sections in the storage container between
    a starting position, in which the metering plunger body is pushed fully into the storage container and
    at least one metering position, in which the metering plunger body is pushed out of the storage container by a distance corresponding to the desired metering amount,
  wherein the metering plunger body is hollow and releases a through opening between
    a plunger body opening, which faces the at least one access opening, and
    a suction opening of the metering plunger body accessible from the outside,
  wherein the metering plunger body has an outer metering sleeve and an inner, hollow plunger body, which is rotatable about a longitudinal axis of the metering device in the metering sleeve,
  wherein the metering sleeve in a metering sleeve bottom facing the access opening of the storage container has at least one metering sleeve opening arranged eccentric to the longitudinal axis,
  wherein the inner plunger body in a plunger body bottom facing the access opening of the storage container comprises a plunger body opening arranged eccentric to the longitudinal axis,
  wherein in a passage relative rotational position of the metering sleeve relative to the inner plunger body there is a passage between the inside of the storage container and the inside of the inner plunger body through the metering sleeve opening and the plunger body opening,
  wherein in a closed relative rotational position of the metering sleeve relative to the inner plunger body the passage between the inside of the storage container and the inside of the inner plunger body through the metering sleeve opening and the plunger body opening is closed.

According to the invention it has been recognized that with the concept of a multi-part metering plunger body there is a new degree of freedom, which can be used in particular to effectively prevent a flow of preparation from the inside of the storage container to the inside of the metering plunger body, if this is not desirable. The flow of preparation from the inside of the storage container to the inside of the metering plunger body can be either prevented or enabled independently of a pressure difference between these two adjoining chambers. The metering device can be configured in principle with only three individual parts, namely the storage container and a two-part metering plunger body with a metering sleeve and an inner plunger body. The formation of a passage opening on rotating the inner plunger body relative to said surrounding metering sleeve makes it possible in the passage relative rotational position to form a passage with a relatively large passage width, which facilitates the use of the metering device after completion of the metering when suctioning the preparation through the suction opening. The dead volume inside the metering device can be reduced compared to known configurations. As long as the metering device is in the closed relative rotational position of the metering sleeve relative to the inner plunger body the metering device can be used like a syringe. By means of the plunger body a flowable preparation can be suctioned into the storage container, like drawing a syringe, and delivered via the access opening in the storage container, for example applied orally.

A locking device comprising a locking device with at least one locking element on the metering plunger body and with at least one counter locking element on the storage container for defining at least two metering locking lift positions of the metering plunger body in the storage container, from the starting position, which positions define the corresponding metering position of the metering plunger body and differ in the distance between the starting position and the respective metering position, enables convenient metering of the preparation.

A configuration of the metering sleeve comprising an inner metering sleeve section, which is guided in a sealed manner in the storage container, and an outer metering sleeve section, which is guided on an outer wall of the storage container, wherein the locking device is arranged in the area of a guide of the outer metering sleeve section on the storage container, enables a compact configuration even if the locking device, e.g. to avoid leakages, is arranged to be separate from sealing faces between the metering plunger body and the storage container. The metering device with the inner and the outer metering sleeve section can be configured in particular along the longitudinal axis of metering device with an advantageously small structural length. The inner and outer metering sleeve section can be arranged to overlap along the longitudinal axis at least in some sections or can also be fully overlapping. The locking device in the area of the outer metering sleeve section can be easily accessible from the outside and configured to be visible in particular from the outside which simplifies the readability during the metering. For example a scale that can be read from the outside can be provided in the area of the locking device.

A one-piece seal formed between the metering plunger body and the storage container on the metering plunger body simplifies the assembly of the metering device and can lead to a reduction of the overall production costs.

A sealing body sealing the metering sleeve bottom against the plunger body base, which in the through relative rotational position provides access between the inside of the storage container and the inside of the inner plunger body, improves the sealing effect between the metering sleeve bottom and the plunger body bottom if the inner plunger body is rotated relative to the metering sleeve in the closed relative rotational position. The sealing body can be designed as a separate component.

A one-way valve in the passage between the inside of the storage container and the inside of the inner plunger body, which allows the flow of preparation from the storage container into the inner plunger body and blocks the flow of preparation in opposite direction, prevents already suctioned preparation from flowing back undesirably from the inside of the inner plunger body into the inside of the storage container.

The function of the aforementioned sealing body and the function of the aforementioned one-way valve can be performed by the same component.

An arrangement of the sealing body and/or the one-way valve in a recess in the metering sleeve bottom enables a compact design.

A rotational guiding, in which a guide of a rotational movement of the outer metering sleeve to the inner plunger body is formed by at least one partly circular elongated hole arranged in circumferential direction about the longitudinal axis, formed in the metering sleeve or in the plunger body and a guiding pin running in the elongated hole formed on the plunger body or on the metering sleeve, enables a clear definition on the one hand of the passage relative rotational position and on the other hand of the closed relative rotational position and a clear definition of a displacement rotational movement of the outer metering sleeve to the inner plunger body between these two rotational positions.

A stop device with a stop body secured axially on the storage container and a counter stop body secured axially on the metering sleeve for determining a metering lock lift position of the metering plunger body in the storage container, which represents a corresponding metering position of the metering plunger body, starting from an inserted starting position of the metering plunger body in the storage container, enables the metering of the preparation without it being necessary to read a scale.

A configuration of the stop device, in which the metering sleeve has an inner metering sleeve section, which is guided in a sealed manner in the storage container, and an outer metering sleeve section, which is guided on an outer wall of the storage container, wherein the stop body is arranged in the area of a guide of the outer metering sleeve section on the storage container, enables an arrangement of the stop body, which is accessible from the outside. In this way the stop body can be adjusted manually to define a metering amount.

The displaceability of the stop body, in which the stop body can be displaced in an elongated hole of the metering sleeve for determining the metering position, is a simple variant for defining a required metering position. The elongated hole can be formed in the outer metering sleeve section of the metering sleeve. One end of the elongated hole can at the same time form the counter-stop body.

A locking configuration, in which the stop body has a locking structure and is displaceable between a release position, in which the locking structure is ineffective, and a locking position, in which the locking structure cooperates with a complementary locking counter structure, which is formed on the storage container, so that in the locking position the stop body is secured axially on the storage container, leads to an axial securing of the stop body. The locking structure and locking counter structure can be formed by toothings or threaded structures or other complementary structures.

Locking devices comprising a first locking device, which secures the stop body surmountably in the release position, and a second locking device, which secures the stop body after surmounting the first locking device in the locking position, enable a defined repositioning of the stop body from the release position into the locking position.

A two-part configuration of the storage container, in which the storage container is in two parts and comprises an inner metering cylinder with a supply volume and an outer guiding sleeve, wherein the metering cylinder and the guiding sleeve are secured axially to one another and, in an axial relative end position, against relative rotation to one another about the longitudinal axis, enables, for example in the production of said components in an injection molding process, a greater degree of freedom with regard to the shaping. The rotation protection against the unwanted rotation of the metering cylinder relative to the guiding sleeve about the longitudinal axis can be provided by a radial groove, which is formed in the metering cylinder or in the guiding sleeve and which engages in a complementary radial rib, which in turn is formed on the guiding sleeve or metering cylinder. The axial securing of the metering cylinder on the guiding sleeve can be formed by a circumferential ring or circumferential rib, which is formed on the metering cylinder or on the guiding sleeve and engages in a complementary circumferential groove, which is formed in turn in the guiding sleeve or in the metering cylinder. Alternatively, the rotational securing of the metering cylinder on the guiding sleeve can be formed by non-rotationally symmetrical and complementary circumferential or end walls of the metering cylinder and/or the guiding sleeve, which are configured in particular as rotational protection wall sections. The axial and rotational protection can be used to define a metering position of the stop body, provided there is a corresponding configuration of the locking structures and locking counter structures for the stop body.

An axial/rotational protection device, which in a first axial position of the metering cylinder to the guiding sleeve allows a relative rotation of the metering cylinder to the guiding sleeve about the longitudinal axis and in a second axial position of the metering cylinder to the guiding sleeve blocks a relative rotation of the metering cylinder to the guiding sleeve about the longitudinal axis, wherein by means of a relative rotation of the metering cylinder to the guiding sleeve in the first axial position a fine definition can be made of an axial position of stop body to the metering cylinder and thereby the metering position of the metering plunger body in the storage container, is simple to use and not expensive to produce. This protection device can in turn comprise a locking device in the form of a circumferential rib, which is configured to be complementary to a circumferential groove.

According to a further aspect the aforementioned objective is achieved by a metering device for the metered administration of a flowable preparation together with a flowable carrier medium, comprising a storage container for the preparation, which communicates with the environment via at least one access opening, with a metering plunger body, which can be moved in a sealed manner at least in sections into the storage container between a starting position, in which the metering plunger body is inserted fully into the storage container and at least one metering position, in which the metering plunger body is pushed up to a distance corresponding to the desired metering amount of the preparation out of the storage container.

In particular the metering plunger body is not hollow, but is configured as a solid body. The metering device is thus configured in the form of a metering syringe, wherein by means of the plunger body the flowable preparation to be metered is suctioned into the storage container and metering positions of the metering plunger body are defined in particular by metering locking lift positions by suitably configured locking and/or stop devices.

According to this additional aspect the metering device can comprise a locking device with at least one locking element on the metering plunger body and with at least one counter locking element on the storage container for providing at least two metering locking lift positions of the metering plunger body in the storage container, from the starting position, which positions define the corresponding metering position of the metering plunger body, which differ in the distance between the starting position and the respective metering position.

According to this further aspect in this case the metering plunger body can comprise an outer metering sleeve and an inner plunger body, which can be rotated about a longitudinal axis of the metering device in the metering sleeve, whereby the metering sleeve has an inner metering sleeve section, which is guided in a sealed manner in the storage container, and an outer metering sleeve section, which is guided on an outer wall of the storage container, wherein the locking device is arranged in an area of a guide of the outer metering sleeve section on the storage container. Alternatively, the metering sleeve can also be connected to the plunger body non-rotatably and in particular in one piece.

The metering device according to the further aspect can comprise a stop device with a stop body secured axially on the storage container and a counter stop body secured axially onto the metering sleeve for defining a metering locking lift position of the metering plunger body in the storage container, which represents a corresponding metering position of the metering plunger body, from an inserted starting position of the metering plunger body in the storage container.

The metering sleeve can thereby comprise an inner metering sleeve section, which is guided in a sealed manner in the storage container, and an outer metering sleeve section, which is guided on an outer wall of the storage container, wherein the stop body is arranged in the area of a guide of the outer metering sleeve sections on the storage container.

The stop body can be displaceable in this further aspect in an elongated hole of the metering sleeve to define the metering position.

In this further aspect of the metering device the stop body can have a locking structure and be displaceable between a release position in which the locking structure is ineffective and a locking position in which the locking structure cooperates with a complementary locking counter structure which is formed on the storage container, so that in the locking position the stop body is secured axially on the storage container.

In this case a first locking device can secure the stop body in a surmountable manner in the release position and a second locking device can secure the stop body after surmounting the first locking device in the locking position.

Also according to another aspect of the metering device the storage container can be in two parts and comprise an inner metering cylinder with a supply volume and an outer guiding sleeve, wherein the metering cylinder and the guiding sleeve are secured to one another axially and in an axial relative end position against rotation relative to one another about the longitudinal axis.

In this case an axial rotation protection device can be provided which allows in a first axial position of the metering cylinder to the guiding sleeve a relative rotation of the metering cylinder to the guiding sleeve about the longitudinal axis and in a second axial position of the metering cylinder relative to the guiding sleeve blocks a relative rotation of the metering cylinder to the guiding sleeve about the longitudinal axis, wherein by means of a relative rotation of the metering cylinder to the guiding sleeve in the first axial position a fine definition of an axial position of the stop body to the metering cylinder and thereby the metering position of the metering plunger body in the storage container can be provided.

The advantages of individual features of this additional aspect of the metering device correspond to those that have already been discussed above in connection with the first explained metering device according to the invention.

An exemplary embodiment of the invention is explained in more detail in the following with reference to the drawings.

DESCRIPTION OF THE PREFERRED EMBODIMENT

Figure 1:
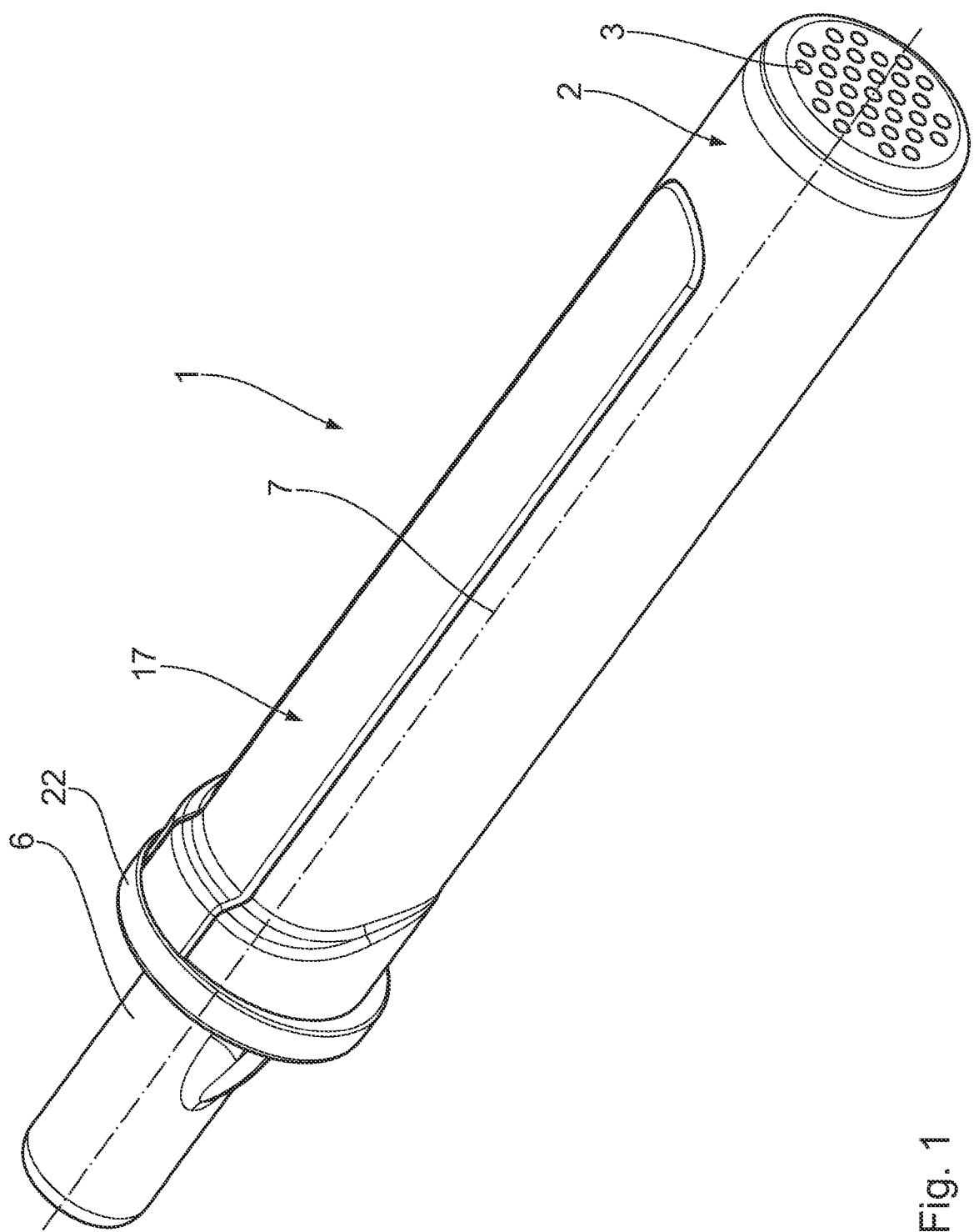
FIGS. 1 and 2 show perspective views of a metering device for the metered administration of a flowable preparation together with a flowable carrier medium.
Figure 2:
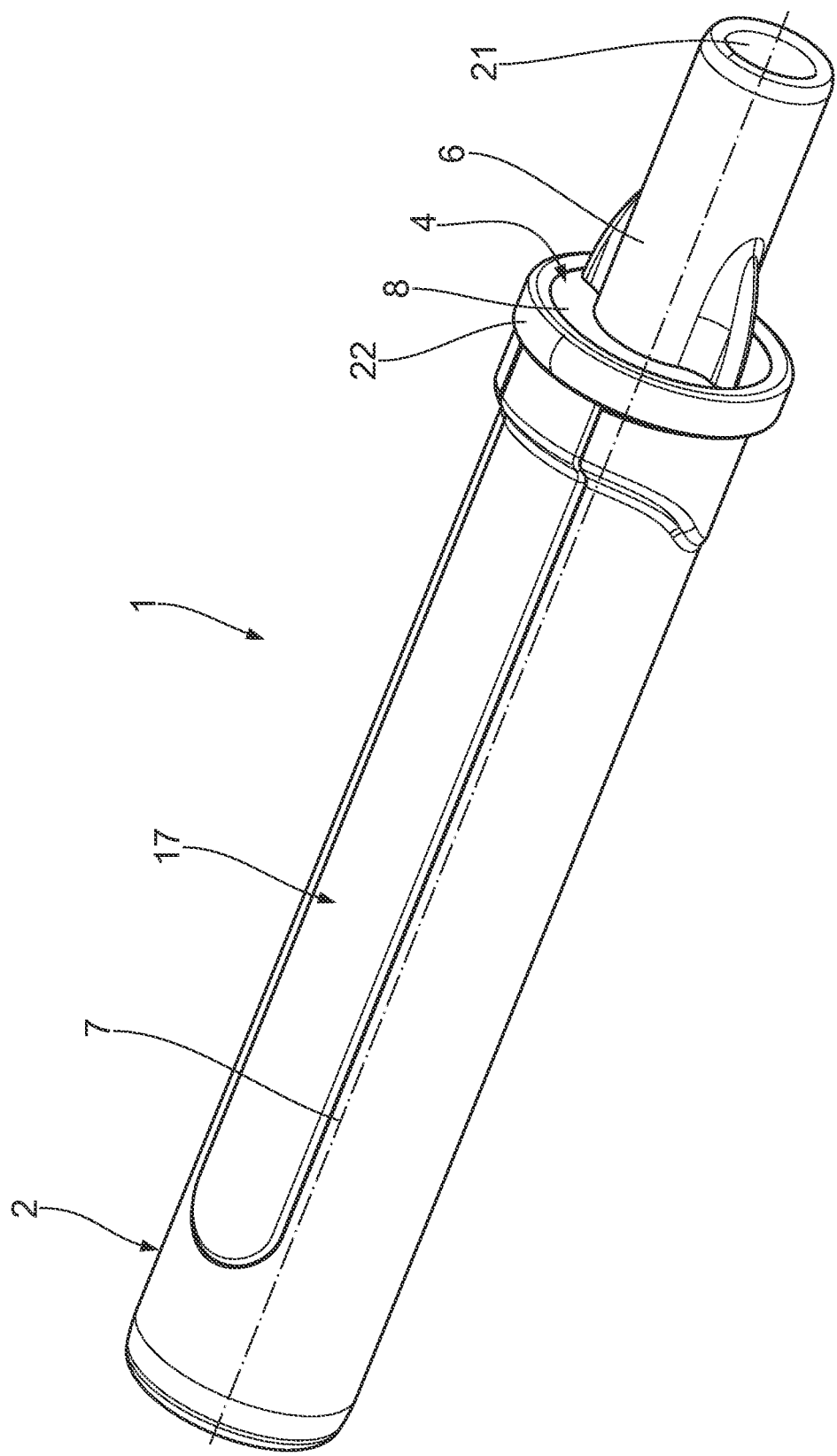

A metering device 1 is used for the metered administration of a flowable preparation together with a flowable carrier medium. All of the components of the metering device 1 are made of plastic.

The metering device 1 has an essentially cylindrical basic form and has an essentially cylindrical storage container 2 for the preparation, which communicates via a plurality of hexagonally grid-like access openings 3 with the environment. Embodiments of the metering device 1 are also possible in which exactly one such access opening 3 or also a different number of such access openings 3 are provided. A metering plunger body 4 is used for metering the preparation. The metering plunger body 4 has an outer metering sleeve 5 and an inner, hollow plunger body 6 as the main components. The inner plunger body 6 is arranged guided rotatably about a longitudinal axis 7 of the metering device 1 in the metering sleeve 5. The rotational guiding for this is formed by a circumferential band 8 of the inner plunger body 6, which can slide in a complementary mount 9 of the metering sleeve 5.

Figure 3:
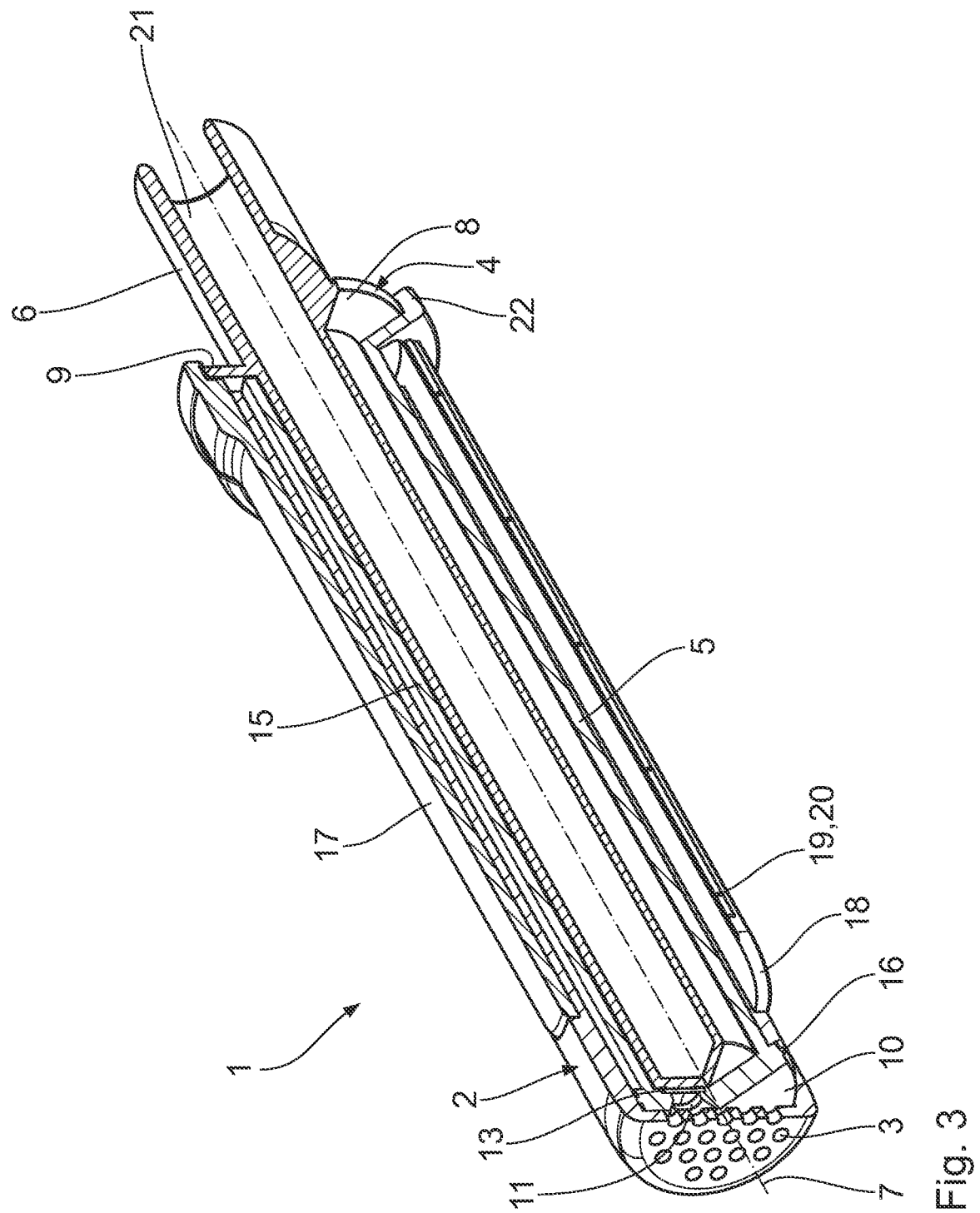
FIG. 3 shows a view of the metering device, which shows the components forming the latter along a longitudinal axis of the metering device in a cut-away form so that internal details of the metering device are visible.

The metering sleeve 5 has in a metering sleeve bottom 10, which faces the access openings 3 of the storage container 2, a metering sleeve opening 11, which is arranged to be eccentric to the longitudinal axis 7. The metering sleeve opening 11 is arranged completely outside the central longitudinal axis 7. The metering sleeve opening 11 is shown in FIG. 3 in cut-away form and is round in the shown metering device 1.

The metering sleeve bottom 10 is sealed against a bottom 12 of the inner plunger body 6 by a sealing body 13, which simultaneously has the function of a one-way valve, as explained further in the following. The sealing body/one-way valve 13 is arranged in a recess 14a of the metering sleeve bottom 10 configured to be complementary to the outer dimensions of the disc-like sealing body/one-way valve 13, which metering sleeve bottom is in alignment with the metering sleeve opening 11.

The inner plunger body 6 has plunger body bottoms 12 facing the access openings 3 of the storage container 2, a plunger body opening 14 arranged eccentrically to the central longitudinal axis 7. The plunger body opening 14 of the inner plunger body 6 is also arranged to be completely outside the central longitudinal axis 7. The plunger body opening 14 is round.

Figure 4:
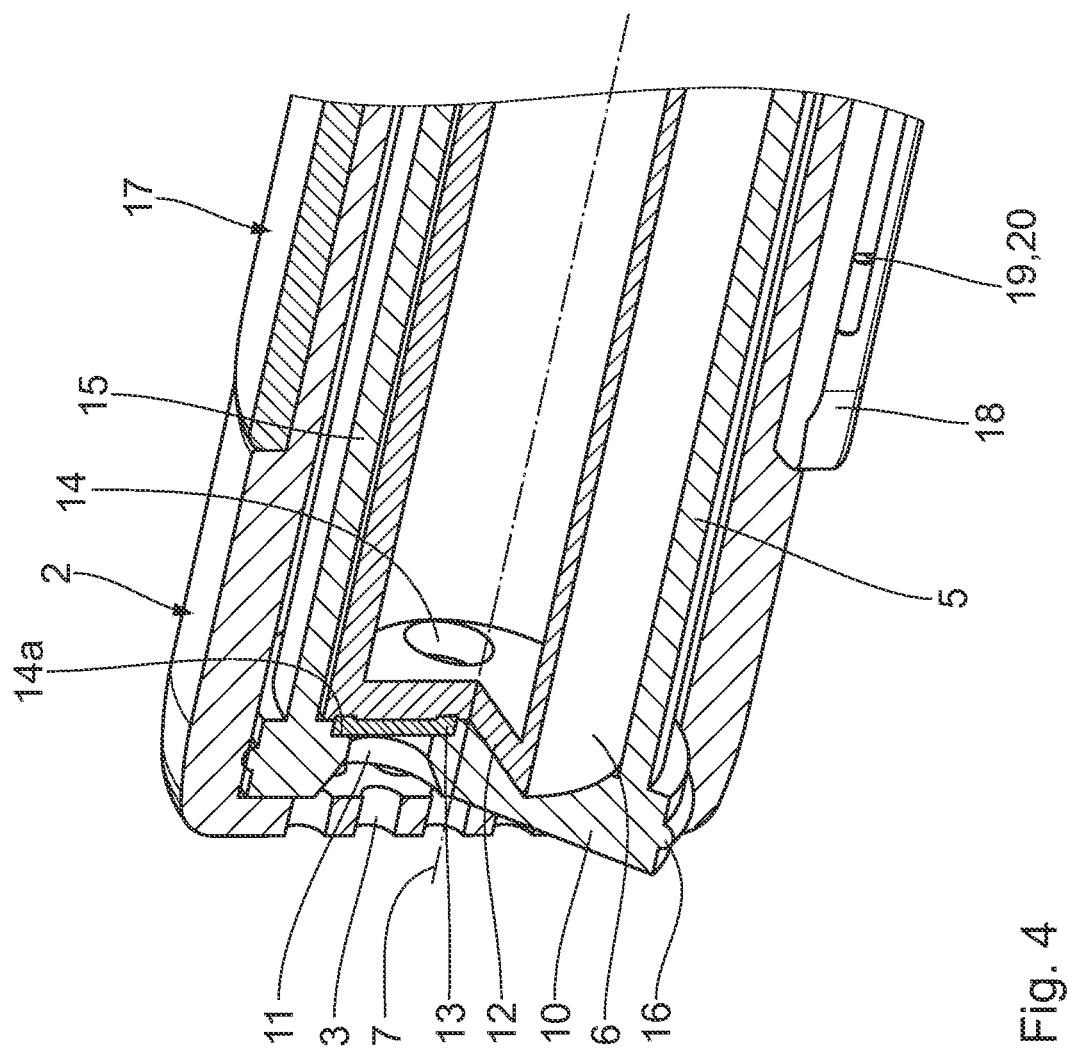
FIG. 4 shows from a different perspective than FIG. 3, but otherwise similar to FIG. 3, a section of the metering device in the area of the bottoms of a storage container, a metering sleeve and an inner plunger body, which both show components of a metering plunger body.
Figure 5:
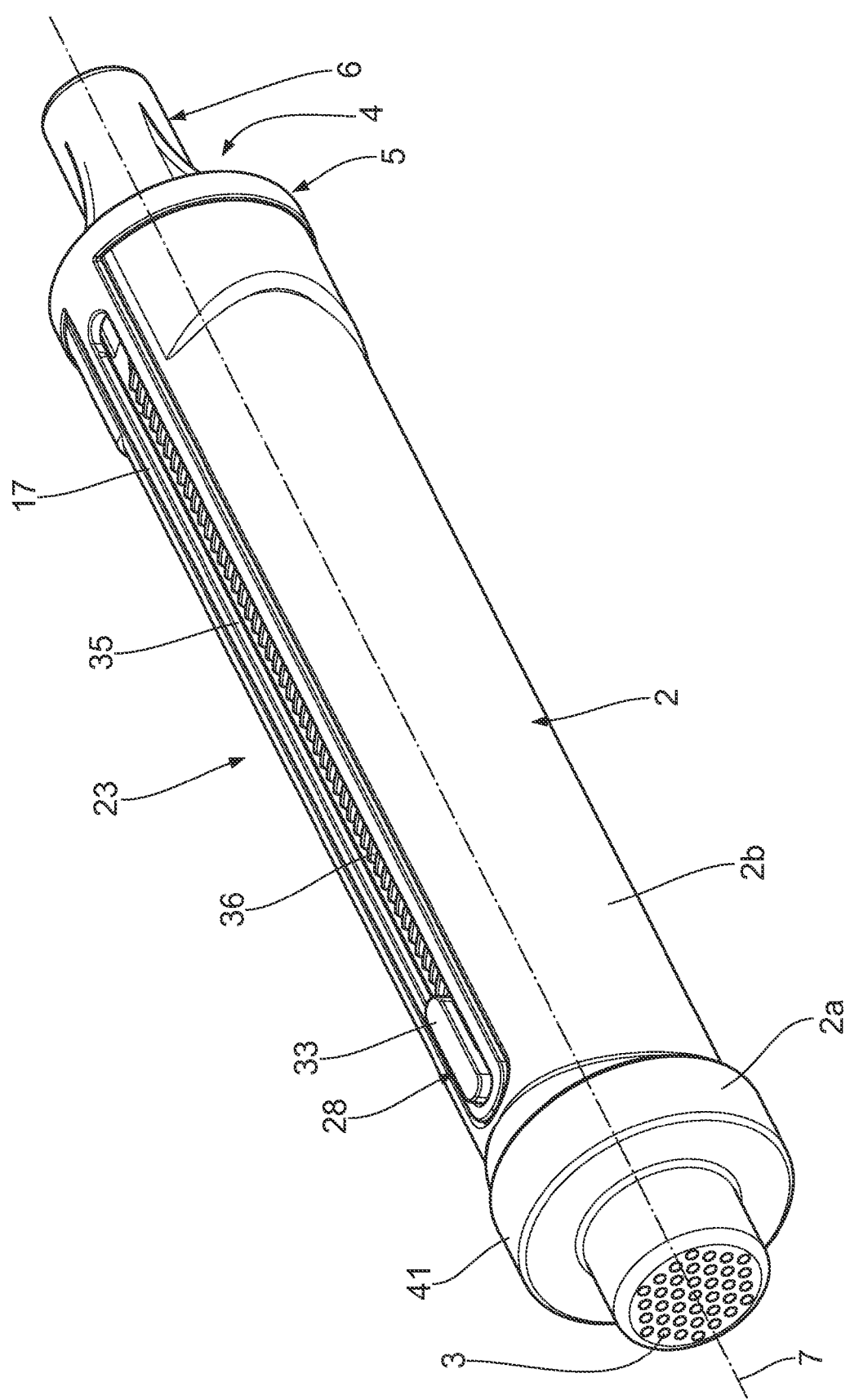
FIG. 5 shows in perspective a further embodiment of a metering device for the metered administration of a flowable preparation together with a flowable carrier medium.
Figure 6:
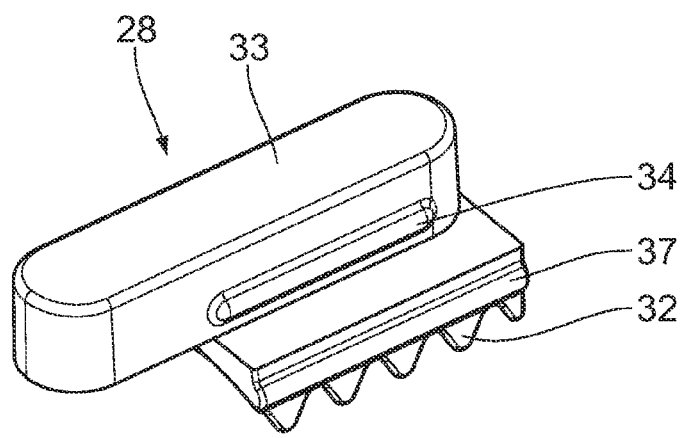
FIG. 6 shows in perspective and enlarged compared to FIG. 5 a stop body of the metering device according to FIG. 5.

The two openings 11, 14 of the metering sleeve 5 on the one hand and the inner plunger body 6 on the other hand are shown in FIG. 4 in a relative rotational position about the central longitudinal axis 7 of the metering sleeve 5 relative to the inner plunger body 6, which is between a through relative rotational position and a closed relative rotational position of the metering sleeve 5 to the inner plunger body 6. In the through relative rotational position of the metering sleeve 5 to the inner plunger body 6 a passage is released for a mixture of the flowable preparation and flowable carrier medium between the inside of the storage container 2 and the inside of the inner plunger body 6 through the metering sleeve opening 11 and through the plunger body 14. In the through relative rotational position the metering sleeve opening 11 is aligned with the plunger body opening 14. In said through relative rotational position the sealing body/one-way valve 13 functions so that a preparation/carrier medium flow is permitted from the storage container 2 to the inner plunger body 6 and a preparation/carrier medium flow is blocked in the opposite direction.

In the closed relative rotational position of the metering sleeve 5 to the inner plunger body 6 a passage between the inside of the storage container 2 and the inside of the inner plunger body 6 is closed. In this position the sealing body/one-way valve 13 has a fully sealing effect between the two bottoms 10, 12, so that no preparation/carrier medium flow is possible between the storage container 2 and the inside of the inner plunger body 6.

The metering sleeve 5 has an inner metering sleeve section 15. In the latter the inner plunger body 6 is arranged between the circumferential band 8 and the plunger body base 12. The inner metering sleeve section 15 is guided in a sealed manner in the storage container 2. For this a seal 16 is used which surrounds the metering sleeve bottom 10 on the casing side and is formed on the latter, which is configured as a lip seal.

An outer metering sleeve section 17 is formed in one piece on the inner metering sleeve section 15, which is formed by two opposite guiding noses 18, which are guided on an outer wall of the storage container. In the area of a guide of the outer metering sleeve section 17, i.e. the two guiding noses 18, a locking device 19 is arranged on the storage container 2. The locking device 19 has locking elements 20 in the form of notches (cf. FIG. 3) on the longitudinal sides of the guiding noses 18 that are opposite one another and run along the longitudinal axis 7 and a counter locking element not shown in the drawing on the storage container 2, which is formed as a locking rib opposite the notches 20 in the outer wall guides of the storage container 2. The locking device 19 is used for defining at least two metering locking lift positions of the metering plunger body 4.

Sealed by means of the seal 16 against an inner wall of the storage container 2, the inner metering sleeve section 15 of the metering sleeve 5 of the metering plunger body 4 in the storage container 2 is sealed displaceably between a starting position shown in the drawing, in which the metering plunger body 4 is pushed completely into the storage container 2, and the different metering positions provided by the locking device 19, in which the metering plunger body 4 is drawn out of the storage container 2 up to distance corresponding to the desired metering amount of the preparation.

The respective metering position is reached when the locking lift position defined by the locking device is reached. The locking device 19 is used to determine the metering locking lift positions of the metering plunger body 4 defined by the locking elements 20 from the starting position, which positions differ in the distance between the starting position and the respective metering position.

The metering device 1 is used in the following manner: firstly a desired metering amount of the preparation is drawn into the storage container 2 of the metering device 1 via the metering plunger body 4. For this the metering device 1 with the end comprising the access openings 3 is dipped into the flowable preparation. Afterwards the metering plunger body 4 is drawn up from the starting position into the desired metering position, which is signaled by the locking device 19 by a corresponding number of clicks produced by the locking elements 20 sliding past the counter locking element.

Said drawing up takes place in the closed relative rotational position of the metering sleeve 5 relative to the inner plunger body 6.

When the preparation has been metered the thus prepared metering device 1 can be dipped into a container with the carrier medium.

Then a user can perform the suctioning at a suction opening 21 of the inner plunger body 6 opposite the plunger body base 2 accessible from the outside. Previously, the user rotates the inner plunger body 6 relative to the metering sleeve 5 into the through relative rotational position. During the suctioning, on the one hand, the preparation provided in the storage container 2 and, on the other hand, the carrier medium are suctioned through the access openings 3, the metering sleeve opening 11, the sealing body/one-way valve 13 and the plunger body opening 14 into the inside of the inner plunger body 6. In the inner plunger body 6 during the flow of the preparation and the carrier medium to the suction opening 21 the preparation is mixed with the carrier medium. This mixture is then suctioned by the user as with a straw.

A relative rotational position of the inner plunger body 6 relative to the outer metering sleeve 5 can be displayed by corresponding text or symbol markings on adjacent visible surfaces of the two components. This relative rotational position display can take place alternatively or additionally by rotational locking which shows the user the respective relative rotational position haptically. To set a required metering amount of the metering device 1 the latter comprises a scale in the area of the guide of the guiding noses 18 in the storage container 2, for example a volume scale.

The inner metering sleeve section 15 and the outer metering sleeve section 17 are connected together by a web section 22, which at the same time delimits the mount 9 for the circumferential band 8 of the inner plunger body 6. Overall the web section 22 has two webs for connecting the inner metering sleeve section 15 with the two guiding noses 18.

In an alternative embodiment the sealing body 13 can also be arranged so that it does not cover the metering sleeve opening 11, but surrounds the latter for example in the form of an O-ring, which seals the metering sleeve bottom 10 against the plunger body bottom 12 of the inner plunger body 6.

In this case the valve function of the sealing body 13 is omitted. The sealing body/one-way valve 13 can also be arranged non-rotatably with the inner plunger body 6, for example in a recess of the latter.

At least one of the two openings 11, 14 can also be configured as an elongated hole curved in circumferential direction.

With reference to FIGS. 5 to 19 in the following a further embodiment of a metering device 23 is described. Components, corresponding to those that have already been described above or with reference to the metering device 1 according to FIGS. 1 to 4 have the same reference numbers and will not be discussed again in more detail.

Also in the metering device 23 the metering plunger body 4 is designed in two parts with the outer metering sleeve 5 and the inner plunger body 6.

Figure 7:
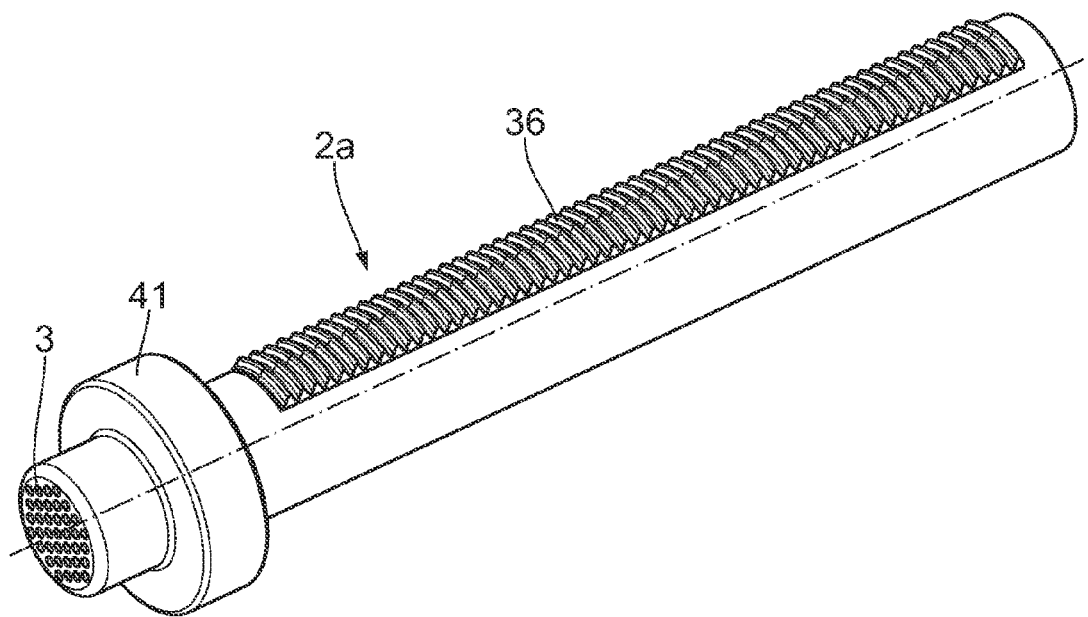
FIG. 7 shows in perspective an inner metering cylinder as part of a two-part storage container of the metering device according to FIG. 5.
Figure 8:
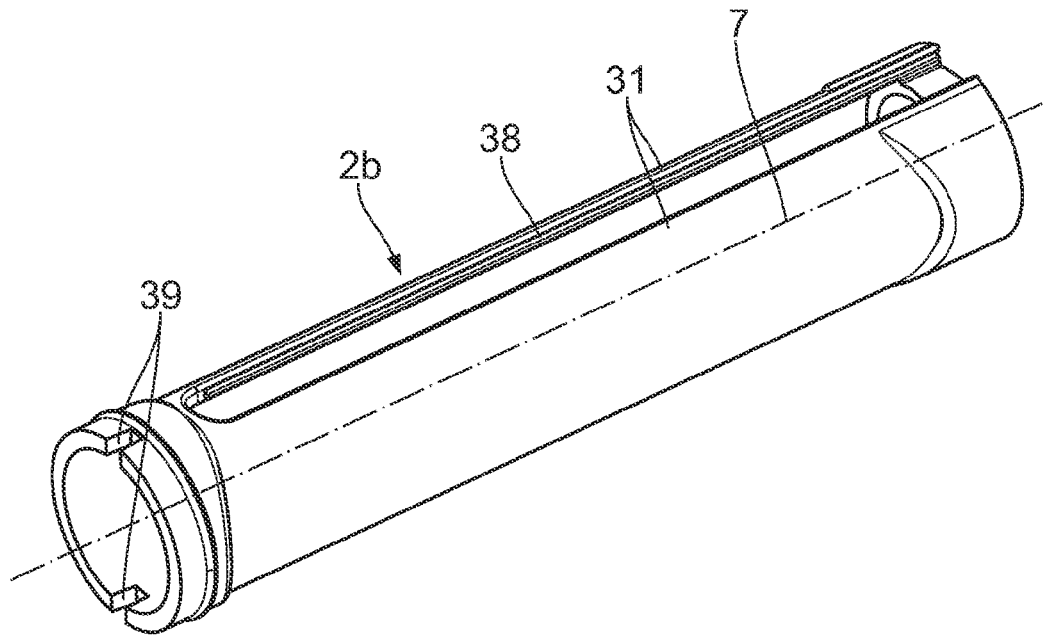
FIG. 8 shows in perspective an outer guiding sleeve of the two-part storage container of the metering device according to FIG. 5.

In the metering device 23 the storage container 2 is configured in two parts and comprises an inner metering cylinder 2a, which is shown in perspective in FIG. 7 and an outer guiding sleeve 2b, which is shown in perspective in FIG. 8. In the inner metering cylinder 2a the supply volume of the storage container 2 is designed for the flowable preparation.

Figure 9:
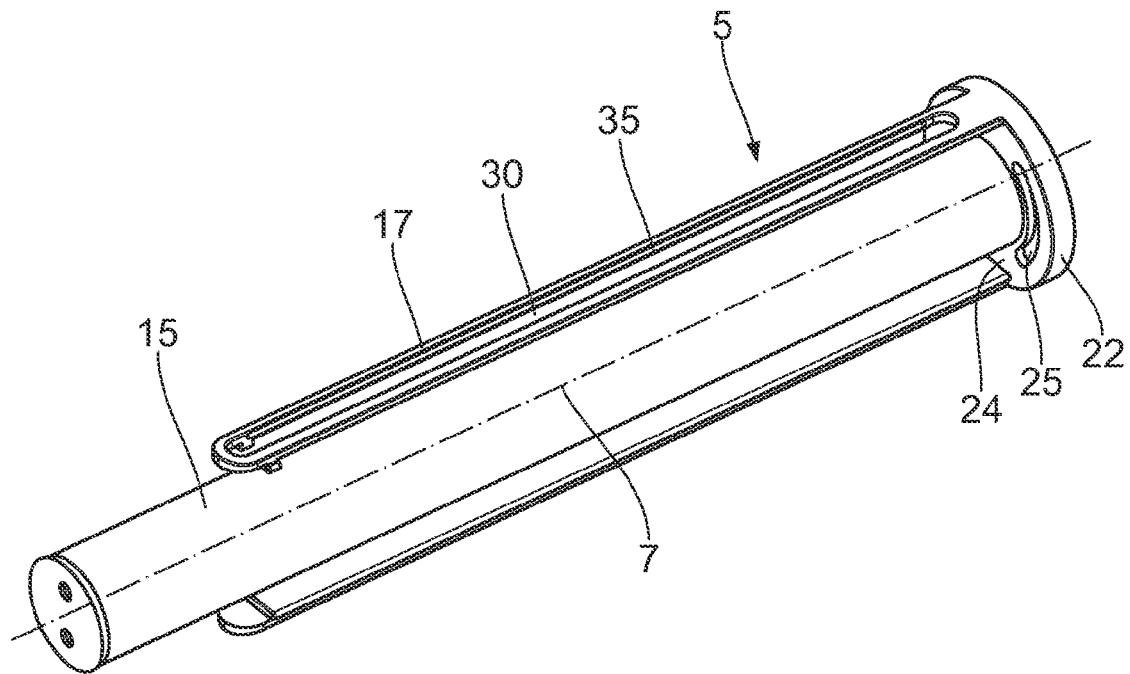
FIG. 9 shows in perspective an outer metering sleeve of a metering plunger body of the metering device according to FIG. 5.
Figure 10:
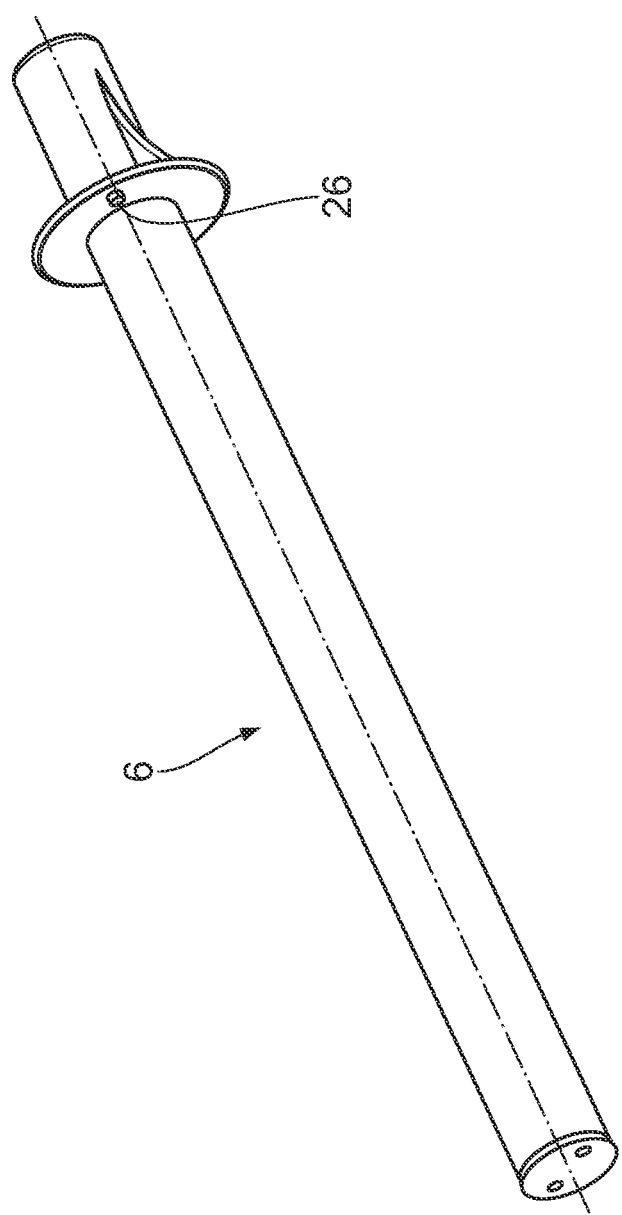
FIG. 10 shows in perspective an inner plunger body of the metering plunger body of the metering device according to FIG. 5.
Figure 11:
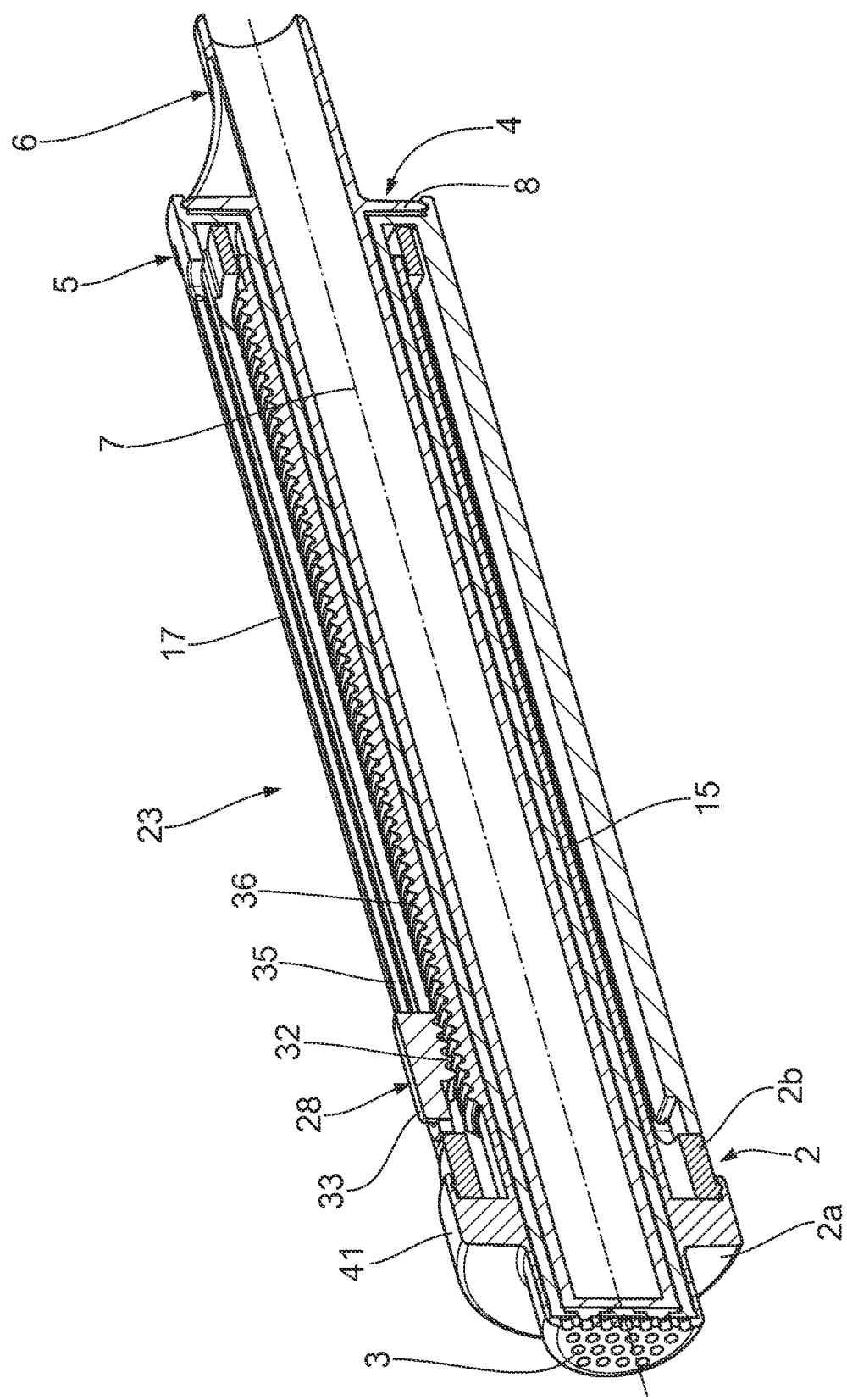
FIG. 11 shows an axial longitudinal cross section of the metering device according to FIG. 5.

In the metering device 23 a guide of a rotational movement of the outer metering sleeve 5, which is shown in perspective in FIG. 9, to the inner plunger body 6, which is shown in perspective in FIG. 10, is formed by an elongated hole pin guide. The latter comprises a partly circular elongated hole 25 arranged in circumferential direction around the longitudinal axis 7 of the metering device 23 in a mouth-piece side annular base plate 24 of the web section 22 of the metering sleeve 5 and a guiding pin 26 running in the elongated hole 25 which is formed on the inner plunger body 6. The guiding pin 26 extends axially spaced apart from the longitudinal axis 7 and parallel to the latter. Also a reverse configuration is possible in which the elongated hole is formed in the plunger body 6 and the guiding pin is formed in the metering sleeve 5.

Figure 19:
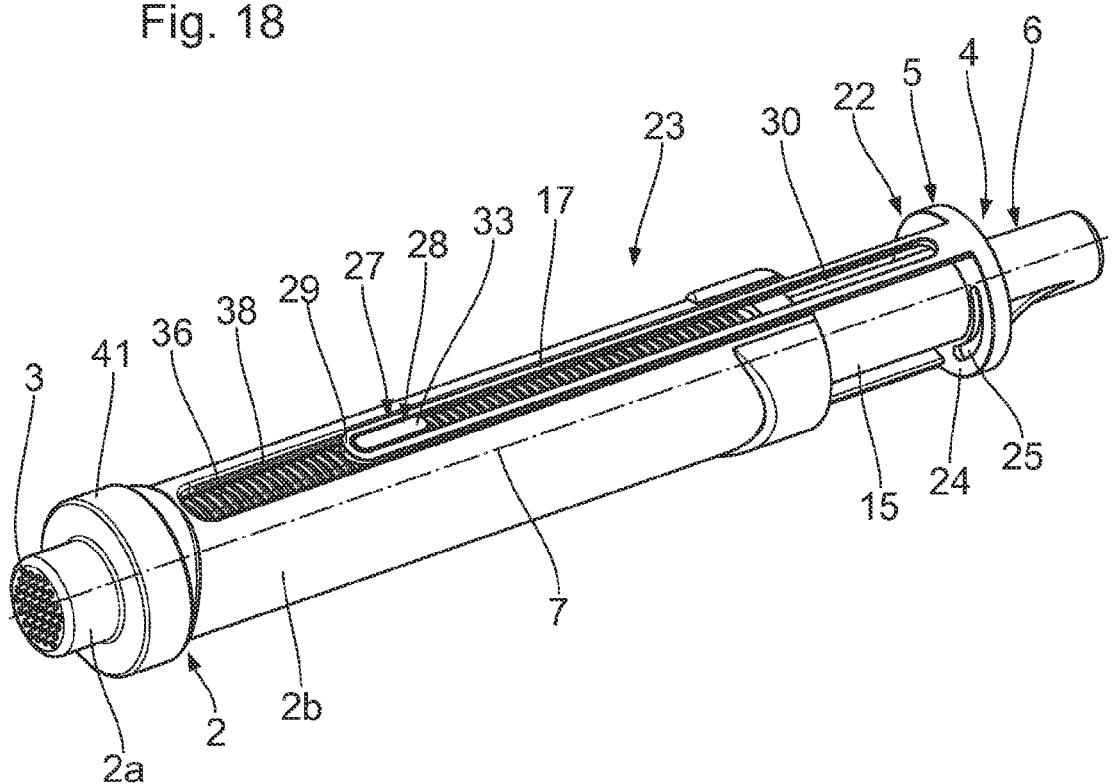
FIG. 19 shows in a perspective view similar to FIG. 5 the metering device according to FIG. 5 in a metering position with the stop body in the locking position.
Figure 20:
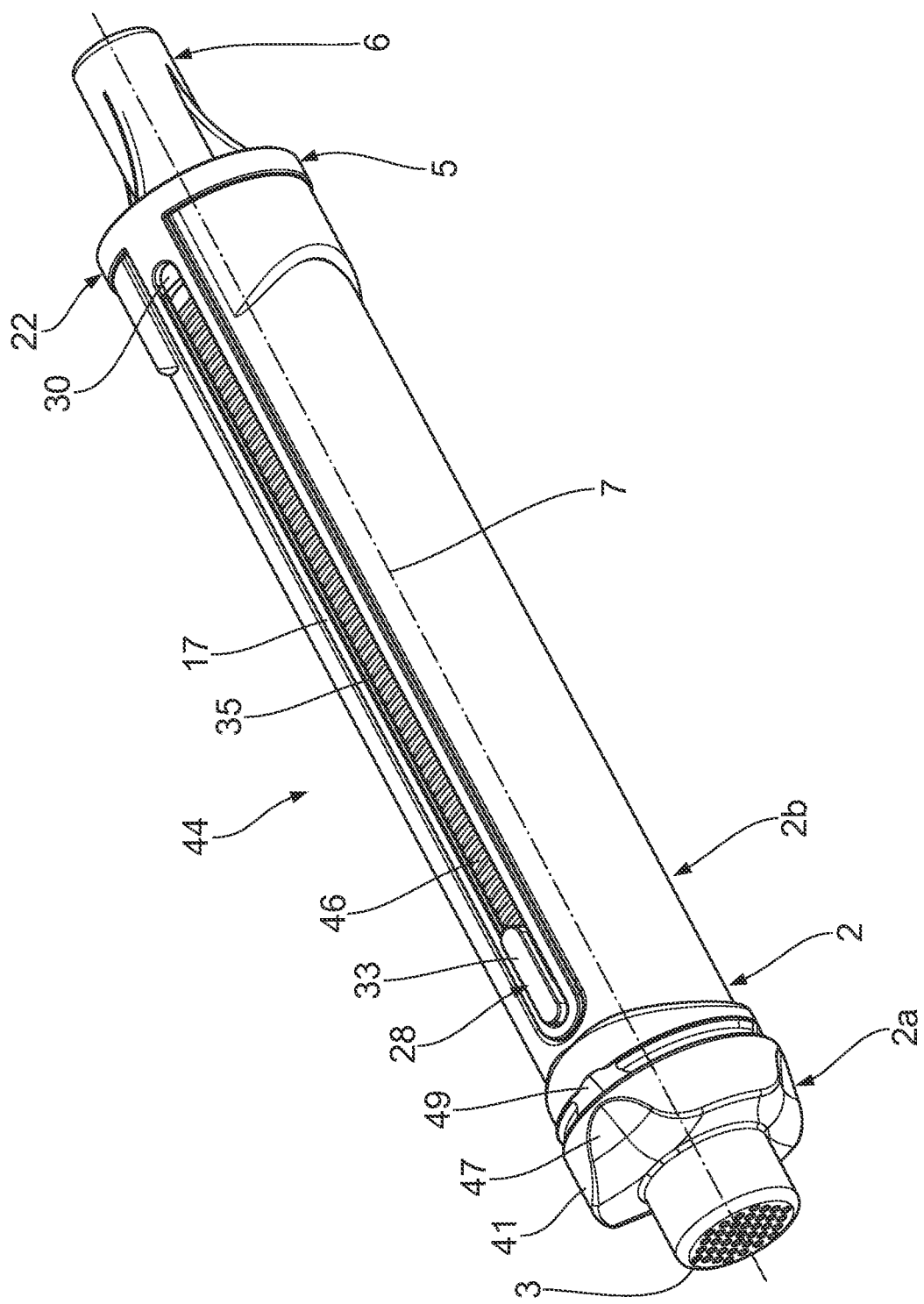
FIG. 20 shows in a view similar to FIG. 5 a further embodiment of a metering device for the metered administration of a flowable preparation together with a flowable carrier medium.
Figure 21:
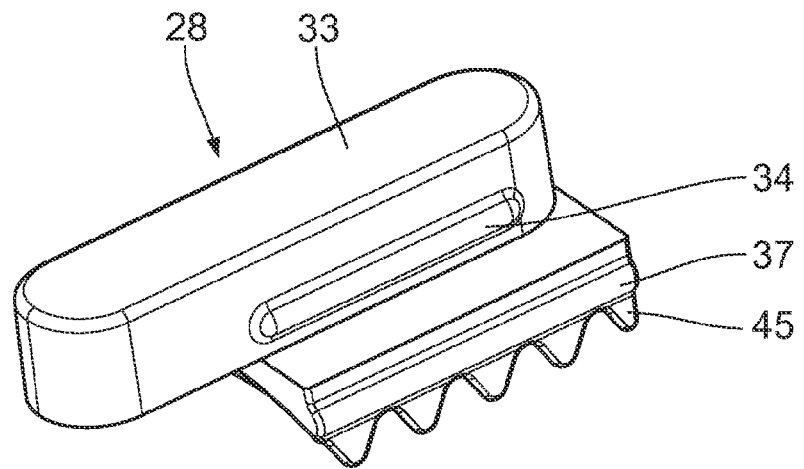
FIG. 21 shows in view similar to FIG. 6 a stop body of the metering device according to FIG. 20.
Figure 22:
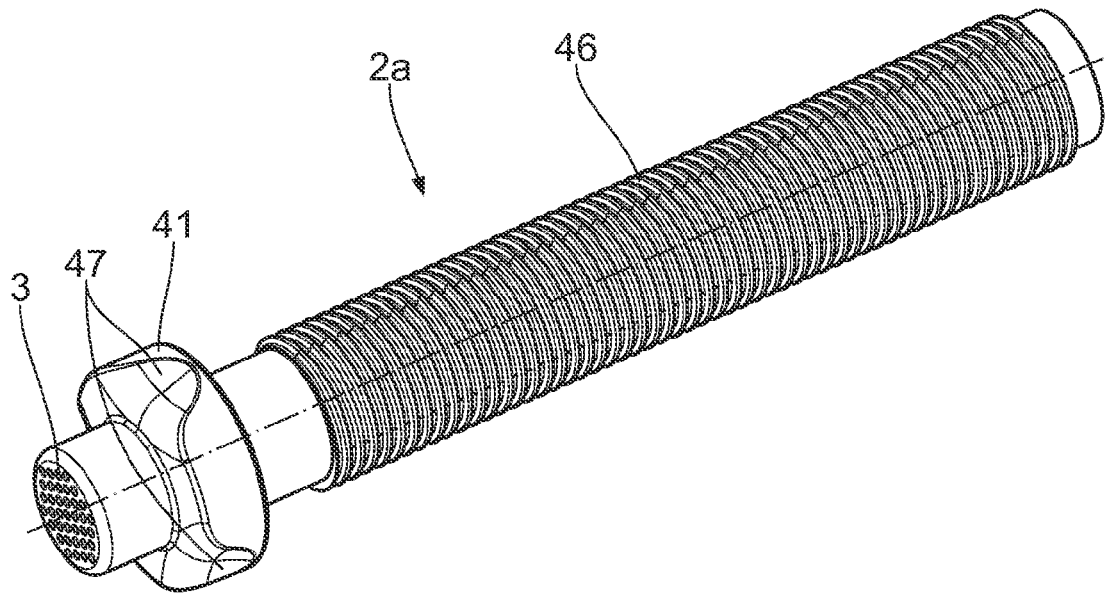
FIG. 22 shows in a view similar to FIG. 7 an inner metering cylinder as part of a storage container of the metering device according to FIG. 20.
Figure 23:
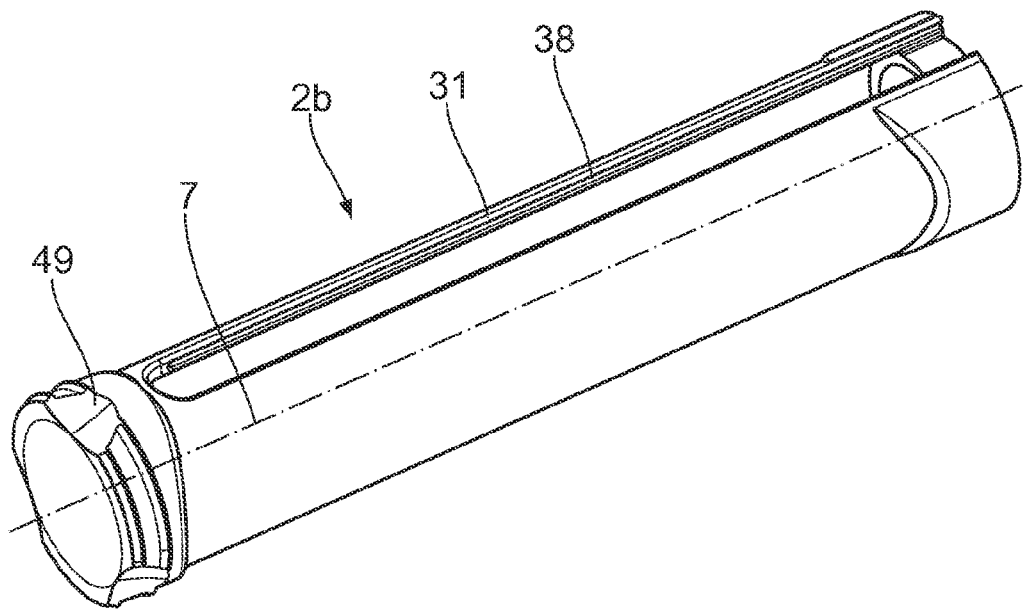
FIG. 23 shows in a view similar to FIG. 8 an outer guiding sleeve as a further part of the storage container of the metering device according to FIG. 20.
Figure 24:
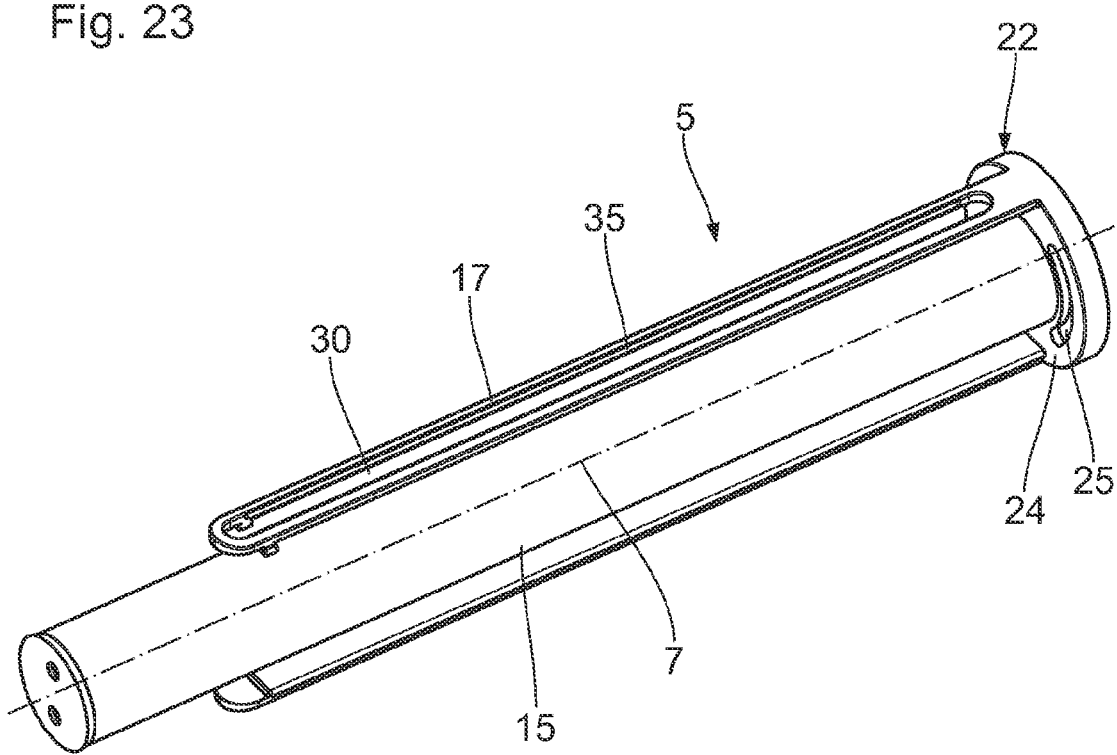
FIG. 24 shows in a view similar to FIG. 9 an outer metering sleeve of a metering plunger body of the metering device according to FIG. 20.
Figure 25:
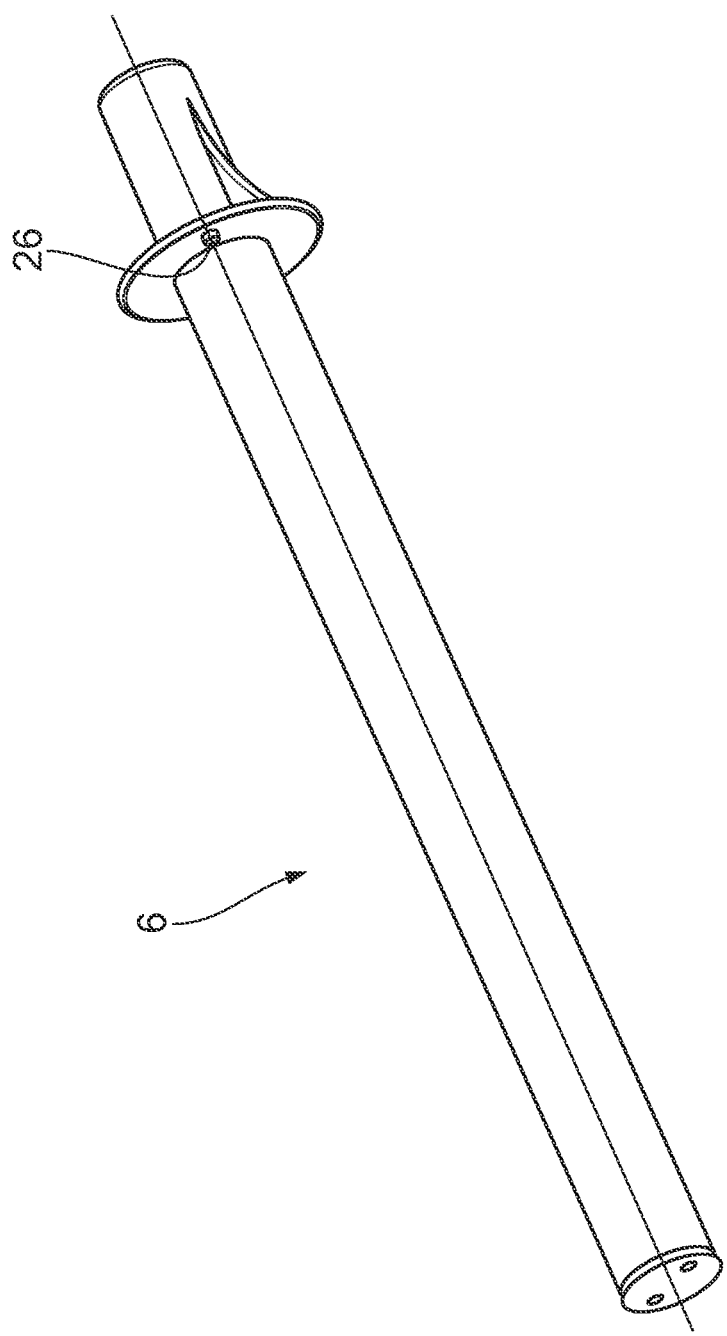
FIG. 25 shows in a view similar to FIG. 10 an inner plunger body of the metering plunger body according to FIG. 20.
Figure 26:
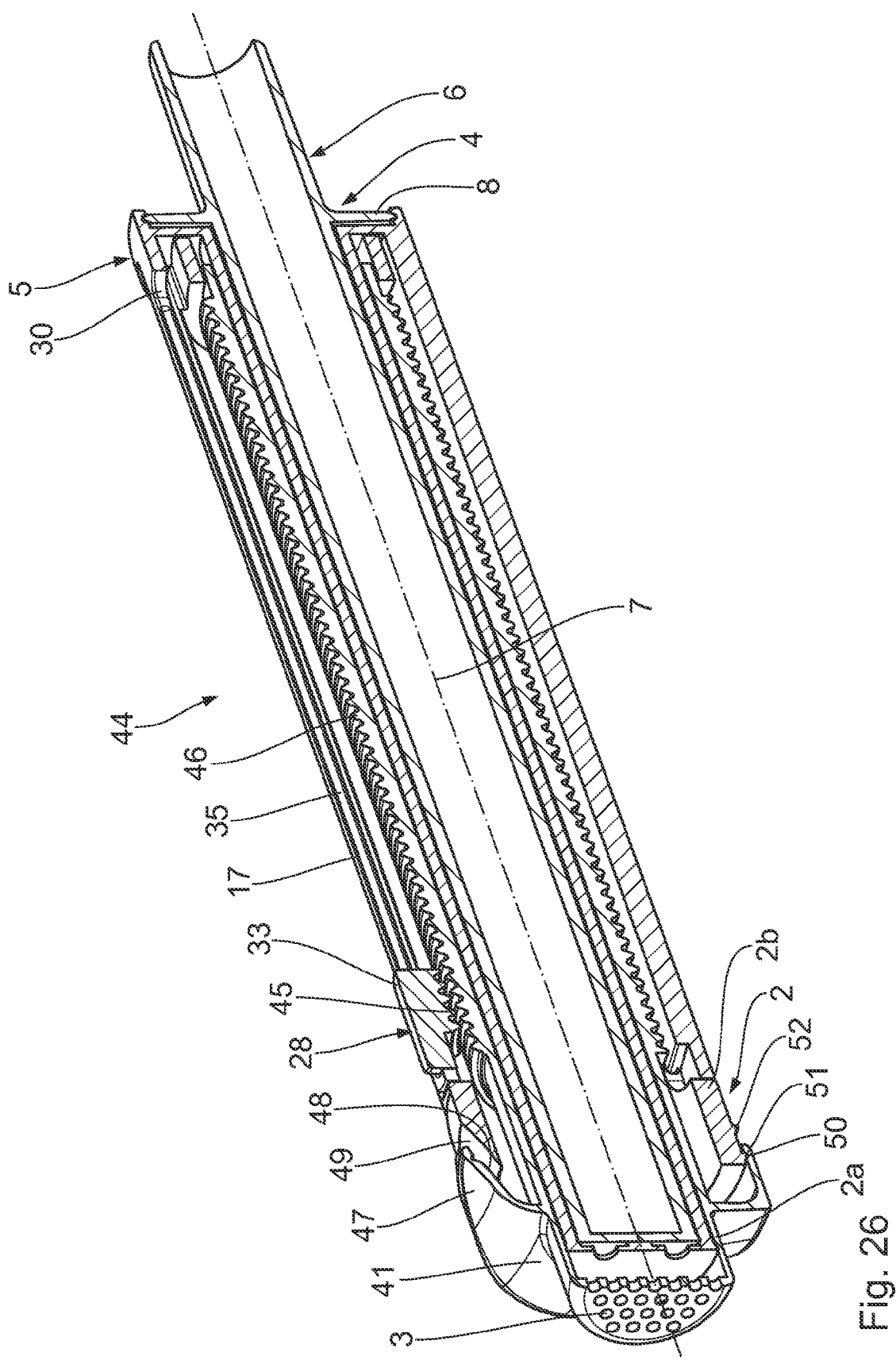
FIG. 26 shows an axial longitudinal cross section of the metering device according to FIG. 20 with the stop body in a release position.

To delimit a metering position of the metering device 23, which is shown in the FIG. 19, the metering device 23 has a stop device 27. The latter comprises a stop body 28, secured axially to the storage container 2 which is shown in perspective in FIG. 6, and a counter stop body 29 secured axially to the metering plunger body 4 in the form of an elongated hole 30 of an outer metering sleeve section 17 of the metering sleeve 5.

The stop device 27 is used to define a specific metering locking lift position from a plurality of selectable metering locking lift positions of the metering plunger body 4 in the storage container 2 of the metering device 1. By means of the stop device 27 a respective metering position of the metering plunger body 4 relative to the storage container 2, e.g. the metering position according to FIG. 19, can be defined from an inserted starting position of the metering plunger body 4 in the storage container 2.

According to the metering device 1 the metering sleeve 5 of the metering device 23 still has the inner metering sleeve section 15 in addition to the outer metering sleeve section 17. The inner metering sleeve section 15 is guided in the storage container 2 in a sealed manner. The outer metering sleeve section 17 is guided, as shown in detail in FIG. 13, on an outer wall 31 of the storage container 2. The stop body 28 is arranged, as clarified in the cross-sectional positions according to FIGS. 16 and 17, in the area of the guiding of the outer metering sleeve section 17 on the outer wall 31 of the storage container 2.

To determine the metering position the stop body 28 can be displaced in axial direction in the elongated hole 30 of the metering sleeve 5. Also during the metering of the metering device 23 the stop body 28 is displaced relative to the elongated hole 30.

Figure 16:
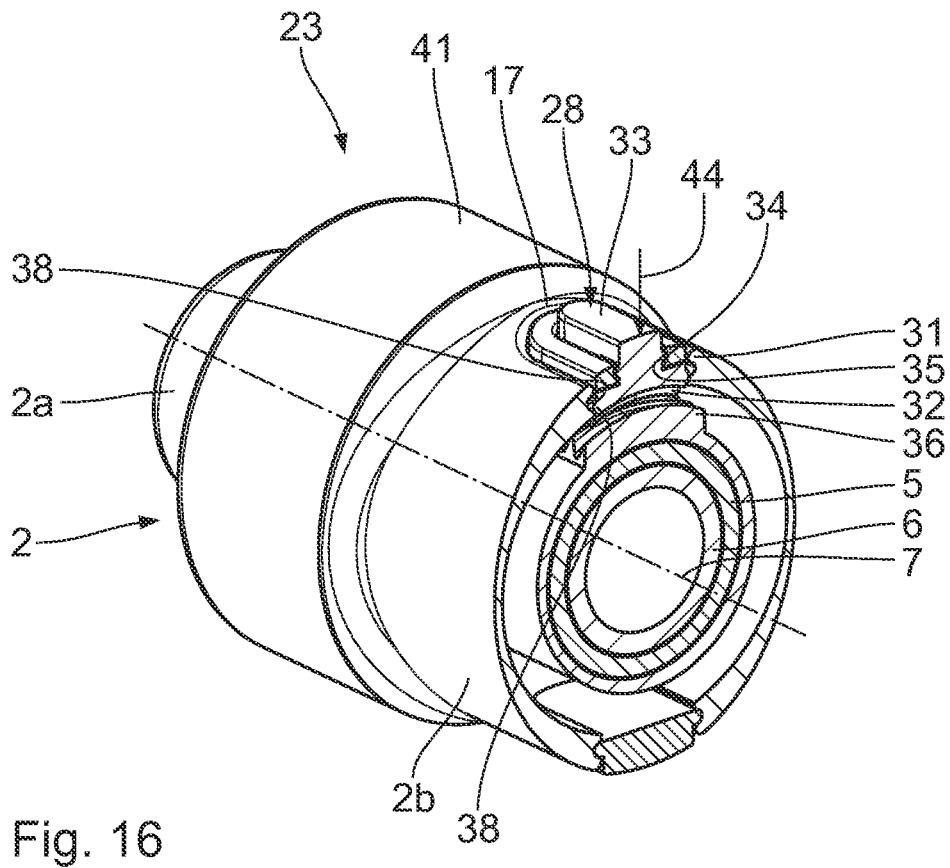
FIG. 16 shows in perspective a cross section of a connecting area of the metering device according to FIG. 5 at the level of the stop body, wherein the stop body is shown in a release position.

During the definition of the metering position the stop body 28 is in a release position, shown in FIG. 16. In the release position a sawtooth-like locking structure 32 of the stop body 28 is ineffective. The locking structure 32 is formed opposite an activating wall 33 of the stop body 28 accessible from the outside and has a tooth direction running perpendicular to the longitudinal axis 7. In the release position of the stop body 28 axial ribs 34 of the stop body 28 are guided in complementary formed axial grooves 35 of the outer metering sleeve section 17.

Figure 17:
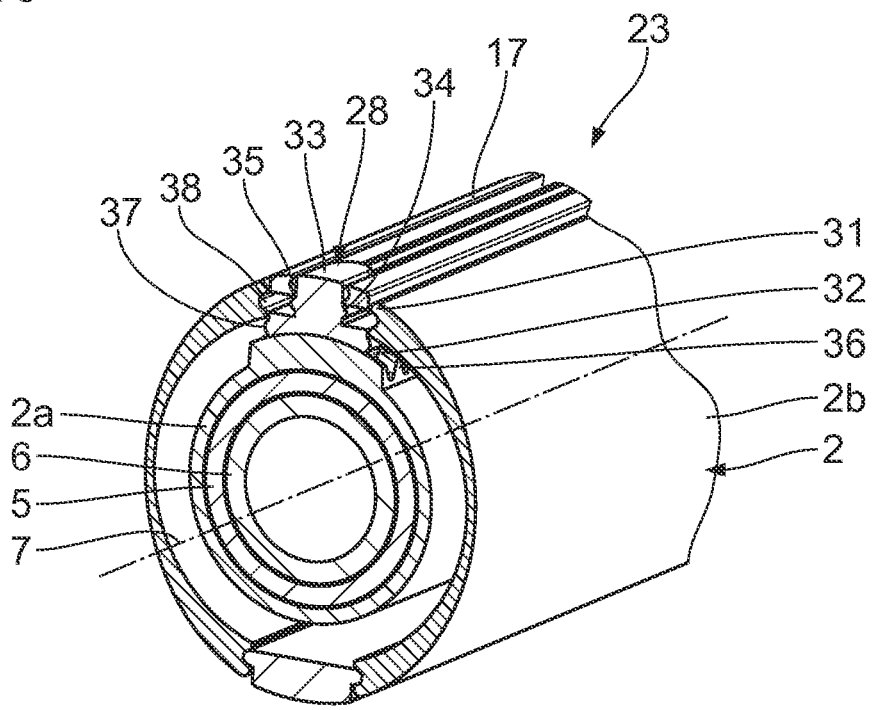
FIG. 17 shows in a perspective cross sectional position similar to FIG. 16 the stop body in a locking position.
Figure 18:
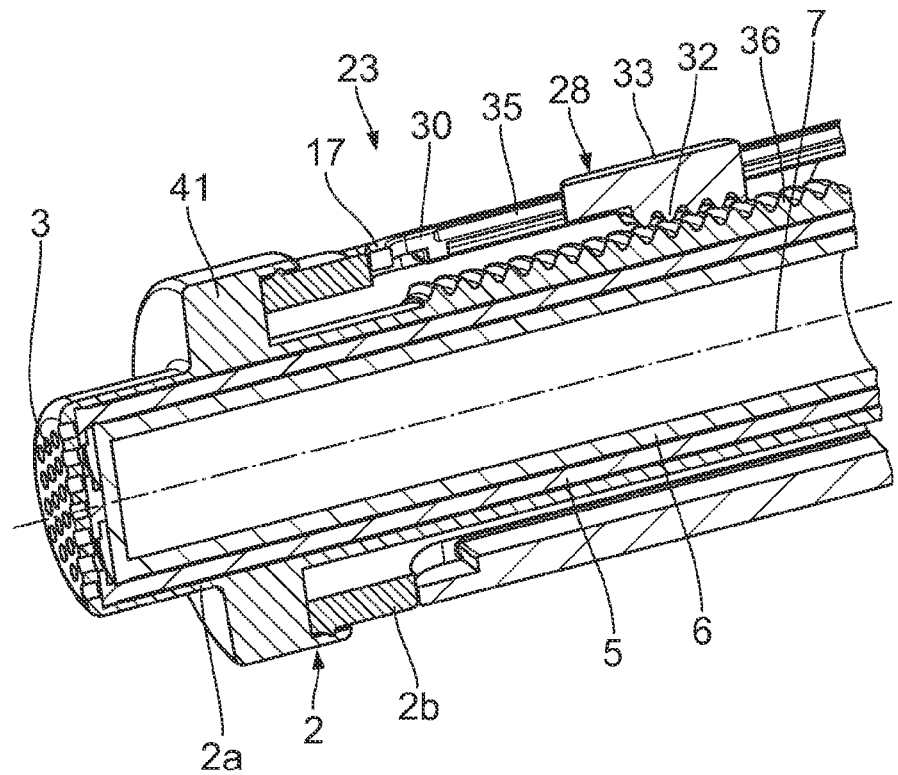
FIG. 18 shows in an axial cross section a cut-out of the metering device according to FIG. 5 in the area of a metering end opposite a mouthpiece, with the stop body in the locking position.

Starting from the release position the stop body 28 can be moved radially to the longitudinal axis 7 into a locking position, which is shown in detail in FIG. 17. In the locking position the locking structure 32 of the stop body 28 acts with a complementary locking counter structure 36 on the inner metering cylinder 2a, which is configured in the metering device 23 as a tooth strip.

In the locking position of the stop body 28 the stop body 28 is secured axially on the storage container 2. In the locking position further axial ribs 37 of the stop body 28 undergrip edge wall delimitations 38 of the outer guiding sleeve 2b, which face the stop body 28.

The stop body 28 spreads from an activating side of the activating wall 33 accessible from the outside towards the locking structure 32 by a step, so that a circumferential extension of the stop body around the longitudinal axis 7 in the area of the locking structure 32 on the one hand is only slightly smaller than the circumferential extension of the tooth strip 36 and on the other hand corresponds approximately to the circumferential extension of the outer metering sleeve section 17.

The axial ribs 34 and the axial grooves 35 form a first locking device which secures the stop body 28 in a surmountable manner in the released position.

The axial ribs 37 and the wall delimitations 38 form a second locking device which secures the stop body 28 after surmounting the first locking device 34, 35 in the locking position.

Figure 12:
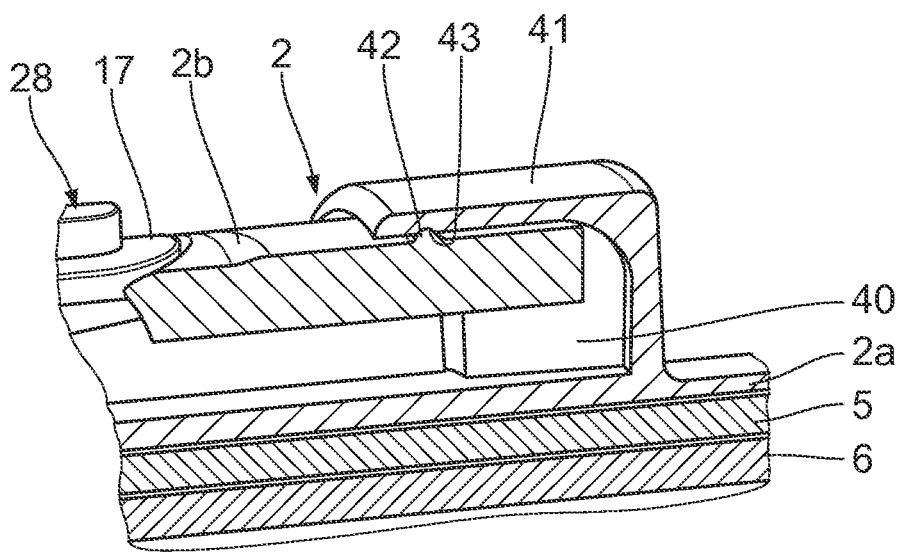
FIG. 12 shows in an enlarged view compared to FIG. 11 and rotated by 180° about a vertical axis a section in the connecting area between the outer guiding sleeve and the inner metering cylinder of the storage container in the area of the positive connection of said two storage container components.
Figure 13:
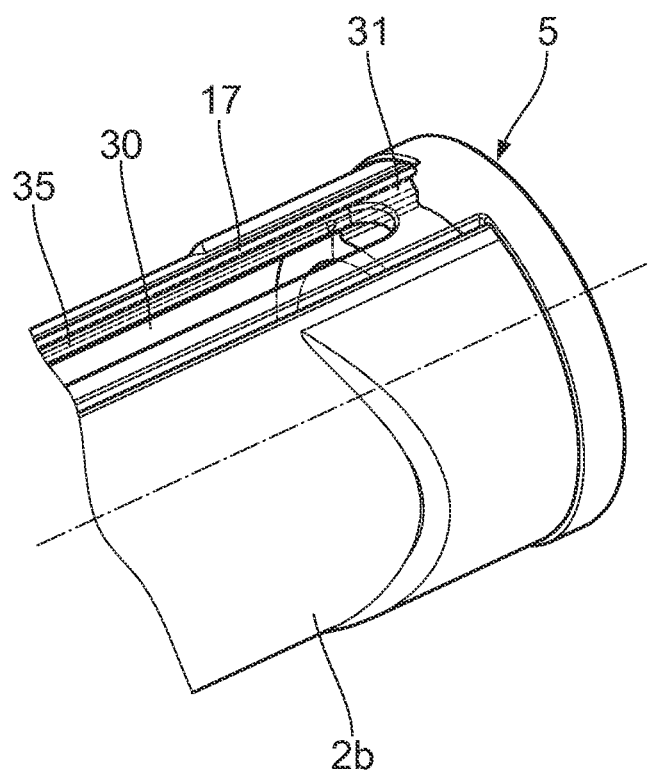
FIG. 13 shows in an enlarged detailed view showing inner details a connecting area between the outer guiding sleeve and the metering sleeve of the configuration according to FIG. 5 in the area of a guide of an outer metering sleeve section on an outer wall of the outer guiding sleeve.
Figure 14:
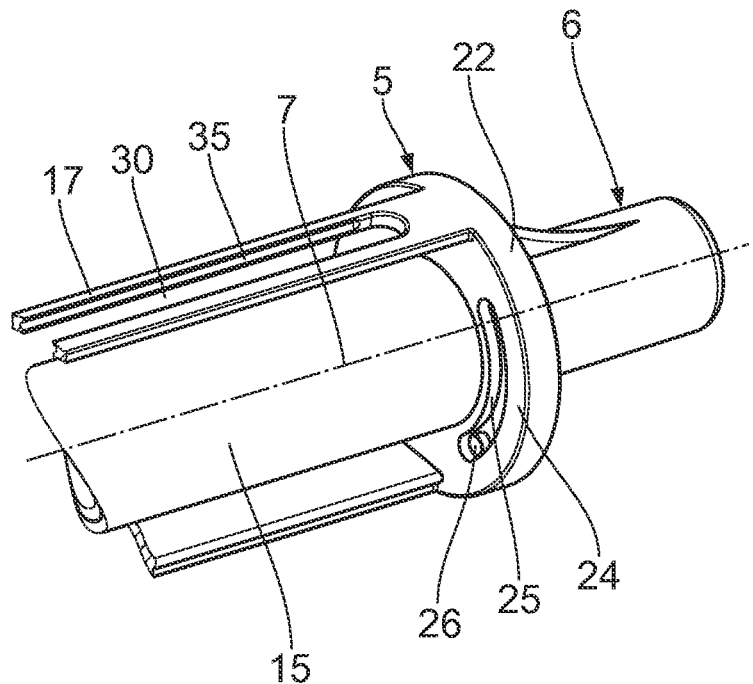
FIG. 14 shows in a perspective section of the embodiment according to FIG. 5 details of a rotational guiding of the outer metering sleeve on the inner plunger body.
Figure 15:
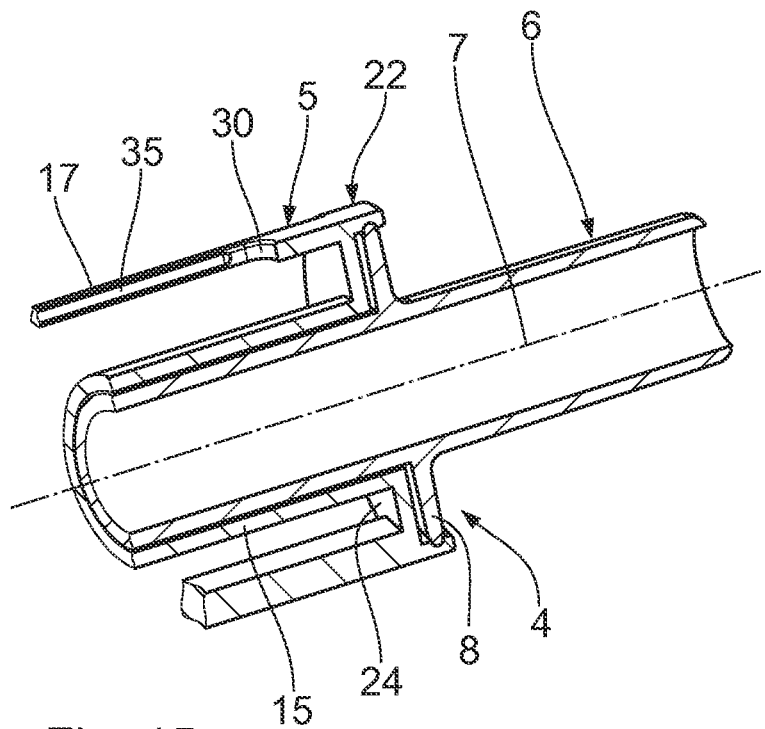
FIG. 15 shows a detail of the guide according to FIG. 14 in axial longitudinal section.

The inner metering cylinder 2a and the guiding sleeve 2b are secured to one another in an axial relative end position, which is shown in detail in FIG. 12, against a relative rotation about the longitudinal axis 7. In addition, the inner metering cylinder 2a and the outer guiding sleeve 2b are secured relative to one another axially.

The rotational protection is provided by two radial grooves 39 (cf. FIG. 8), which are formed at the end facing the access openings 3 in the outer guiding sleeve 2b and engage in complementary radial ribs 40 which are formed on the inner metering cylinder 2a in the area of an annular cap 41 gripping over the end of the guiding sleeve 2b. The axial protection of the inner metering cylinder 2a on the outer guiding sleeve 2b is provided by an outer circumferential rib 42, which is formed on the outer guiding sleeve 2b and engages in a complementary inner circumferential groove 43.

In an alternative not shown embodiment the radial rib 40 is formed on the guiding sleeve 2b and the radial groove 39 in the metering cylinder 2a.

The metering device 23 is used in the following way: firstly by means of the stop device 27 the desired metering amount can be defined, i.e. the metering position which can be reached via the stop. For this the stop body 28 is moved axially in the release position so far relative to the inner metering cylinder 2a and its locking counter structure 36 until the desired metering lift is reached. Afterwards a radial force is exerted on the activating wall 33 of the stop body 28 (cf. force arrow 44 in FIG. 16). The stop body thereby overcomes the first locking device 34, 35 and engages in the locking position, which is secured by the second locking device 37, 38. Then from the metering plunger body 4 inserted completely into the storage container 2, the desired metering amount of the preparation is suctioned into the storage container 2, as already explained above in connection with the metering device 1. The drawing up of the metering plunger body 4 is performed until the stop is reached by the stop device 27, thus until the stop body 28 cooperates with the counter stop body 29, i.e. the end of the elongated hole 30. When the preparation has been metered the thus prepared metering device 23 can be dipped in the container with the carrier medium and administrated, as already explained above in connection with the metering device 1. Alternatively, the metering device 23 can also be used like a syringe after the metering of the preparation. The metered preparation can thus be pushed out as with a syringe by inserting the metering plunger body 4 from the supply volume of the storage container 2.

In the following with reference to FIGS. 20 to 33 a further embodiment of a metering device 44 is explained. Components corresponding to those that have already been explained above with reference to the metering devices 1 and 23 have the same reference numbers and will not be discussed in more detail.

The stop body 28 (cf. FIG. 21) of the metering device 44 has a locking structure 45, which is configured to be complementary to a locking counter structure 46 of the inner metering cylinder 2a of the metering device 44 in the form of a thread.

A rotation protection against a relative rotation of the inner metering cylinder 2a relative to the outer guiding sleeve 2b is formed in the metering device 44 by non-rotationally symmetrical and complementary circumferential or end walls of the inner metering cylinder 2a and the outer guiding sleeve 2b. For this the annular cap 41 of the inner metering cylinder 2a in circumferential direction has a plurality of indentations 47 which extend in an inner wall of the annular cap 41 of the inner metering cylinder 2a to an end-side end area of the guiding sleeve 2b. In this way inner rotation protection wall sections 48 of the annular cap 41 of the inner metering cylinder 2a are formed. Complementary thereto the end side end area of the guiding sleeve 2b has outer rotation protection wall sections 49.

Figure 27:
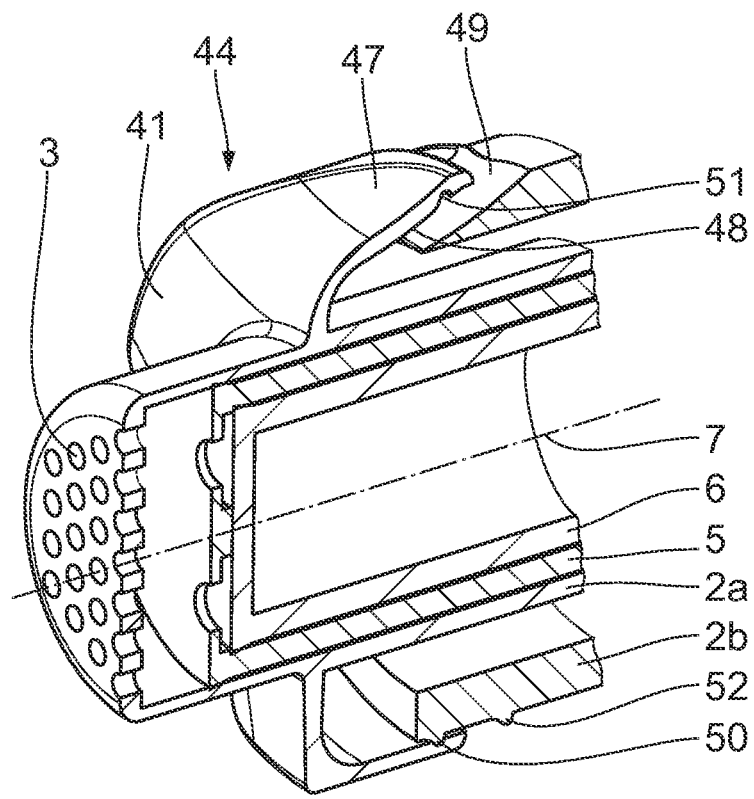
FIG. 27 shows a section enlargement of FIG. 26 in the connecting area of the inner metering cylinder to the outer guiding sleeve of the storage container, wherein an axial protection device is shown in a first axial position of the metering cylinder to the guiding sleeve, in which a rotation of the metering cylinder relative to the guiding sleeve is permitted.
Figure 28:
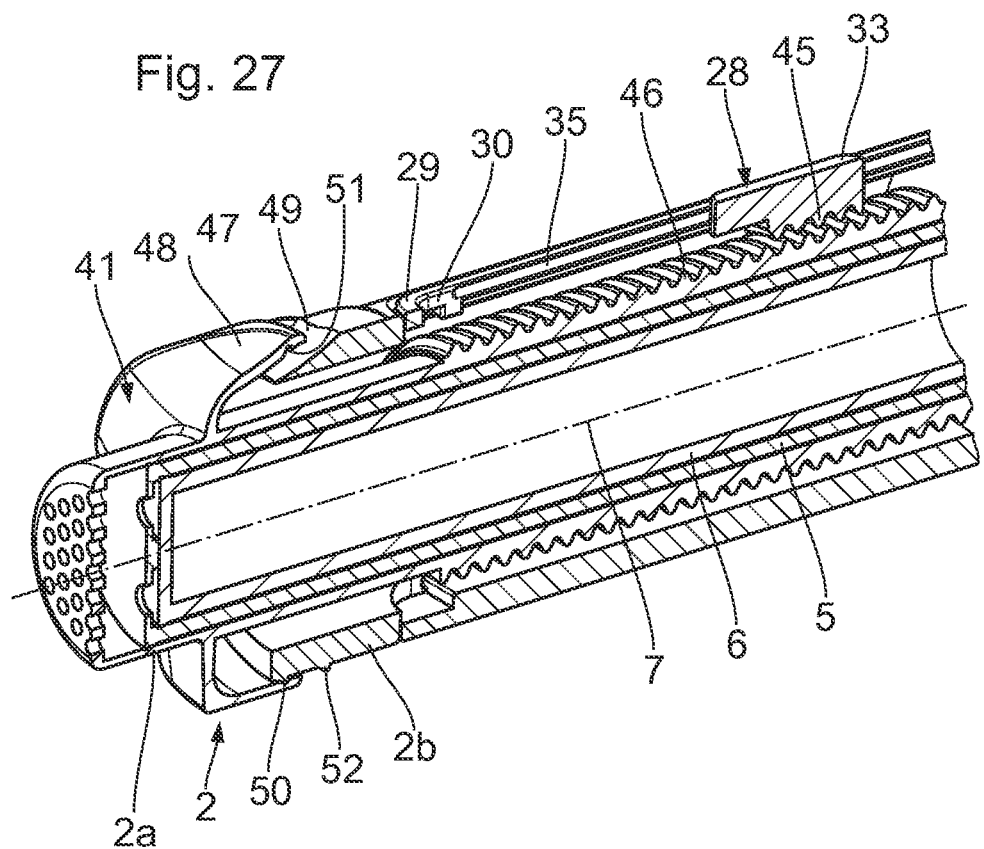
FIG. 28 shows the metering device according to FIG. 20 in a view similar to FIG. 18 with the stop body in the locking position.
Figure 29:
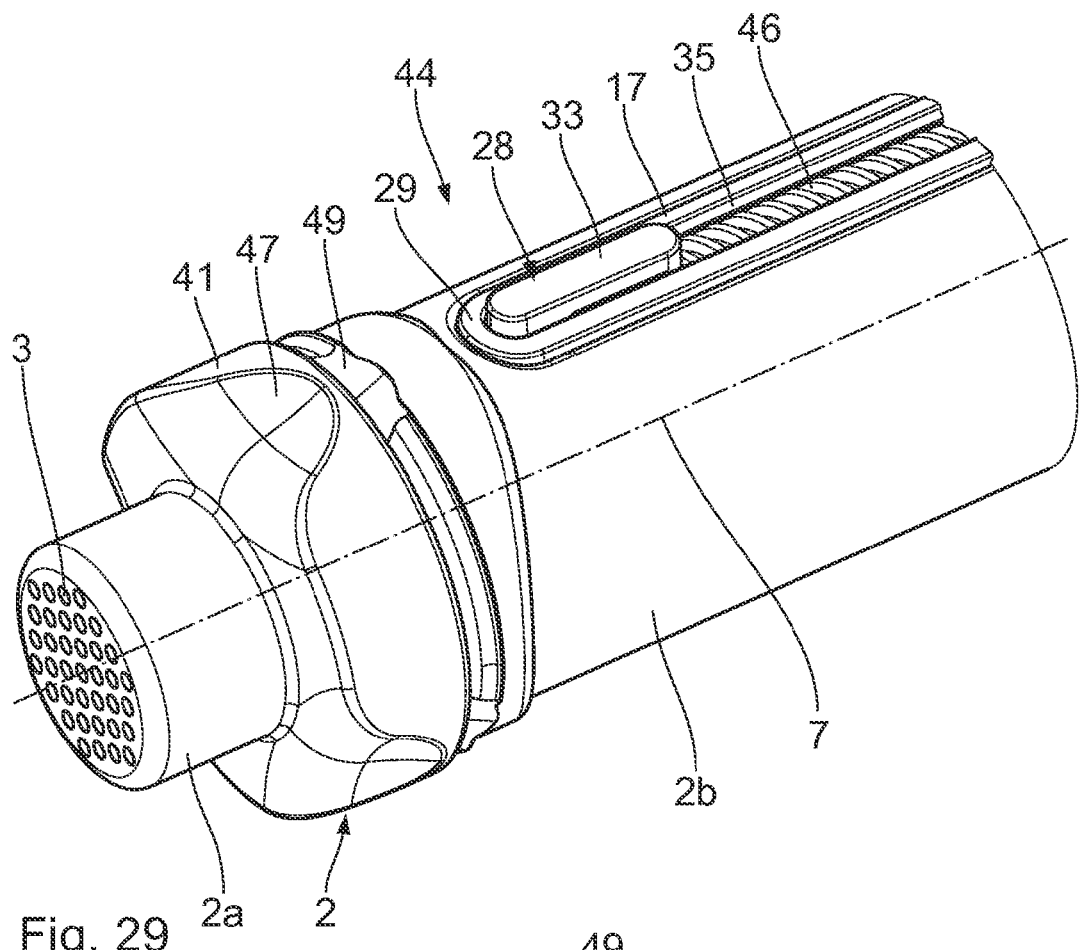
FIG. 29 shows in perspective a metering end of the metering device according to FIG. 20 with the stop body in the locking position and the axial protection device in the first axial position.

FIG. 27 shows the guiding sleeve 2b in an axial position relative to the metering cylinder 2a. In the latter the two rotation protection wall sections 48, 49 come free from one another sufficiently so that a relative rotation of the metering cylinder 2a relative to the guiding sleeve 2b is possible about the longitudinal axis 7. The axial position according to FIG. 27 is secured axially by a circumferential rib 50, which is formed on the end-side end area of the guiding sleeve 2b and which engages in a complementary circumferential groove 51 in the free end section of the annular cap 41 of the metering cylinder 2a. In the released axial position according to FIG. 27 a relative rotation of the metering cylinder 2a to the guiding sleeve 2b is possible.

Figure 30:
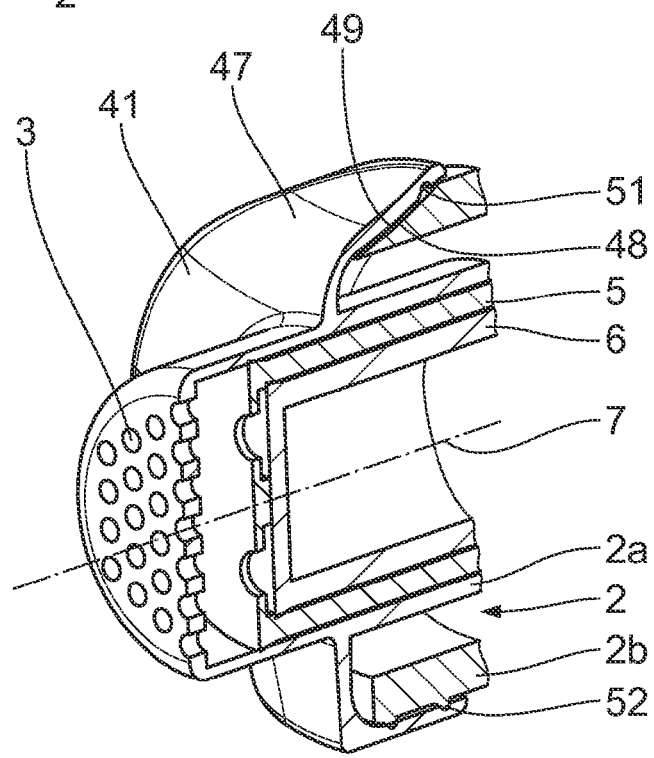
FIG. 30 shows in a view similar to FIG. 27 the axial protection device in a second axial position of the metering cylinder to the guiding sleeve, in which compared to the first axial position the guiding sleeve is inserted into the metering cylinder and in which a rotation of the metering cylinder relative to the guiding sleeve about a longitudinal axis of the metering device is blocked.
Figure 31:
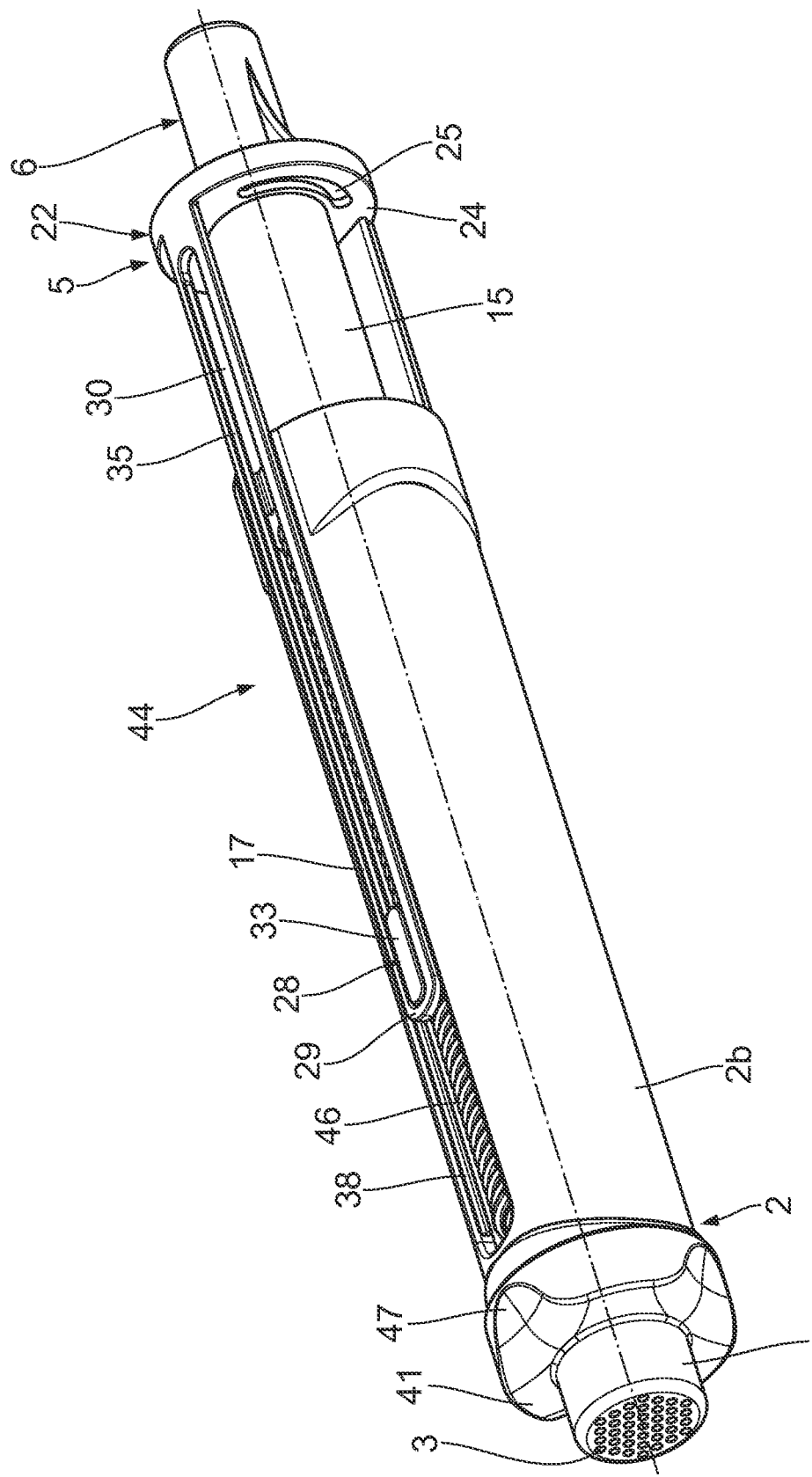
FIG. 31 shows in a view similar to FIG. 19 the metering device according to FIG. 20 in the metering position.

FIG. 30 shows a further axial position of the metering cylinder 2a relative to the guiding sleeve 2b, which is reached from the axial position according to FIG. 27 by pushing the guiding sleeve 2b into the annular cap 41 of the metering cylinder 2a. In this further axial position according to FIG. 30 a relative rotation of the metering cylinder 2a to the guiding sleeve 2b about the longitudinal axis 7 is blocked, the non-rotationally symmetrically formed rotation protection wall sections 48, 49 lie against one another directly. The axial position according to FIG. 30 is secured axially by a further circumferential rib 52, which engages in this further axial position into the circumferential groove 51 of the annular cap 41.

The components 48 to 52 together represent an axial/rotation protection device of the metering device 44.

Figure 32:
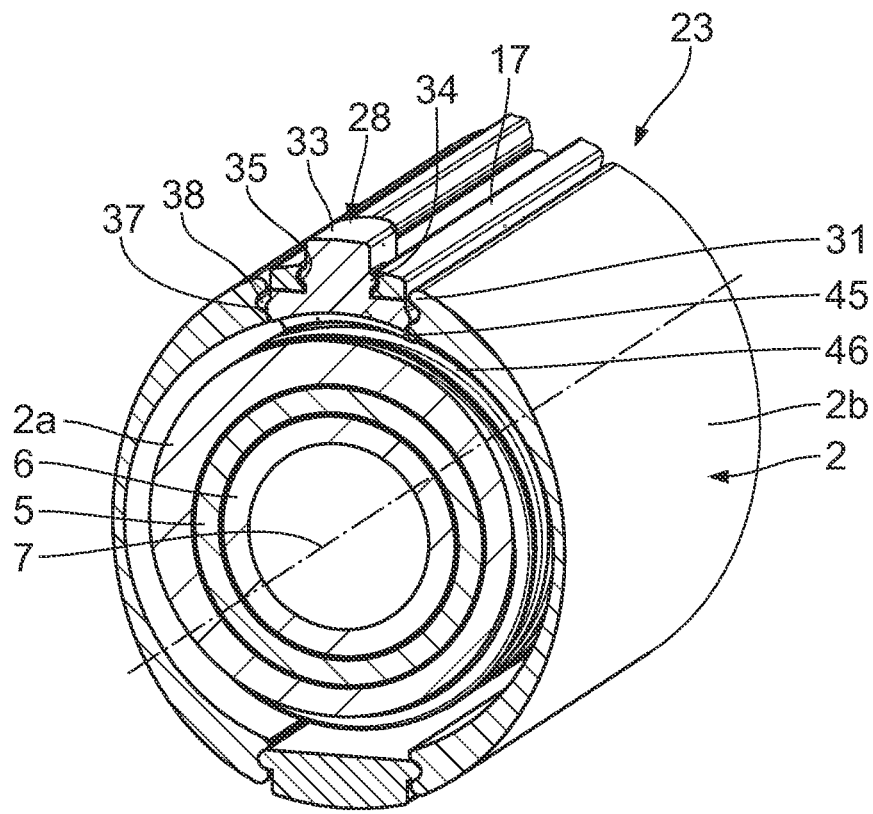
FIG. 32 shows in a view similar to FIG. 16 the stop body of the metering device according to FIG. 20 in the release position.
Figure 33:
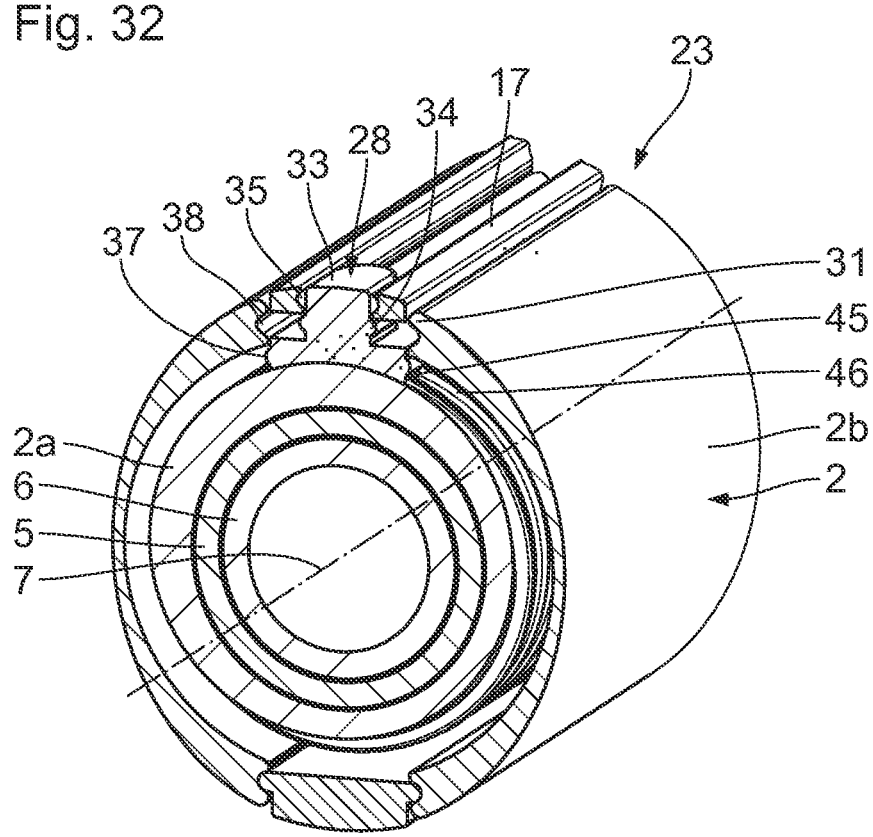
FIG. 33 shows in a similar position to FIG. 17 the stop body of the metering device according to FIG. 20 in the locking position.

During the definition of an axial position of the stop body 28 the latter is first roughly preadjusted in the metering device 44 for handling the metering device 23 in an axial position relative to the storage container 2 and then moved from the release position, shown e.g. in FIG. 32, into the locking position, shown in FIG. 33. During this preparation of the axial position of the stop body 28 the metering cylinder 2a and the guiding sleeve 2b of the storage container 2 are in the axial position according to FIG. 27. After the rough definition of the axial position of the stop body 28 the metering cylinder 2a is then rotated relative to the guiding sleeve 2b about the longitudinal axis 7. By means of the screw effect of the locking structure 45 with the locking counter structure 46 the stop body is displaced finely in axial direction relative to the guiding sleeve 2b, so that a fine positioning of the axial position of the stop body 28 is performed. By means of this thread adjustment also an erroneous definition of the axial position of the stop body 28 can be corrected. After adjusting the axial position of the stop body 28 the rotation protection wall sections 48, 49 are moved to coincide with one another in circumferential direction and the guiding sleeve 2b is pushed completely into the metering cylinder 2a. In this case the circumferential rib 50 disconnects from the circumferential groove 51 and the guiding sleeve 2b is pushed in axial direction into the annular cap 41 of the metering cylinder 2a until the circumferential rib 52 moves into the circumferential groove 51. The two circumferential ribs 50, 52 on the one hand and the circumferential groove 51 on the other hand are configured so that is it easier to overcome the thereby formed locking connections in the insertion direction of the guiding sleeve 2b into the annular cap 41 of the metering cylinder 2a than remove the guiding sleeve 2a from the metering cylinder 2a. The ribs 50, 52 are designed to have a cross section inclined in relation hereto and the groove 51 complementary thereto.

The drawing up of the preparation and the administration of the preparation correspond in the metering device 44 to the method explained above with regard to the metering devices 1 and 23.

The components of the metering devices 1, 23 and 44 explained above are made of plastic.

Insofar as locking connections have been described above which are formed by complementary rib/groove configurations, the rib/groove configurations can also be switched over on the relevant components.

In an alternative variant the metering device 1 is configured as a metering syringe with a plunger 6 formed as a solid body. The hollow chamber on the inside of the metering plunger body 4 and also the suction opening are then omitted. The metering plunger body 4 can be connected in one piece with the outer metering sleeve 5 in this variant. Also the through opening between the plunger body opening 14 and the suction opening 21 is omitted in this metering syringe variant, which is provided in the embodiments explained above in connection with FIGS. 1 to 33. The metering syringe variant can comprise components for determining a metering position of the plunger 6 in the storage container 2 which were explained above in connection in particular with the locking device 19 and the stop device 27 and in connection with the axial/rotation protection device 48 to 52.

The invention claimed is:

1. A metering device for the metered administration of a flowable preparation together with a flowable carrier medium, comprising:
  a storage container for the preparation, which communicates with the environment via at least one access opening,
  a metering plunger body, which is displaceable in a sealed manner at least partially in the storage container between
    a starting position, in which the metering plunger body is pushed fully into the storage container and
    at least one metering position, in which the metering plunger body is pushed out of the storage container by a distance corresponding to a desired metering amount,
  wherein the metering plunger body is hollow and provides a through opening between
    a plunger body opening, which faces the at least one access opening, and
    a suction opening of the metering plunger body accessible from the outside,
  wherein the metering plunger body has an outer metering sleeve and an inner, hollow plunger body, which is rotatable about a longitudinal axis of the metering device in the metering sleeve,
  wherein the metering sleeve in a metering sleeve bottom facing the access opening of the storage container has at least one metering sleeve opening arranged eccentric to the longitudinal axis,
  wherein the inner plunger body in a plunger body bottom facing the access opening of the storage container comprises a plunger body opening arranged eccentric to the longitudinal axis,
  wherein in an open relative rotational position of the metering sleeve relative to the inner plunger body a passage is opened between the inside of the storage container and the inside of the inner plunger body through the metering sleeve opening and the plunger body opening, wherein, in the inner plunger body, during the flow of the preparation and the carrier medium to the suction opening, the preparation is mixed with the carrier medium, wherein in a closed relative rotational position of the metering sleeve relative to the inner plunger body the passage is closed between the inside of the storage container and the inside of the inner plunger body through the metering sleeve opening and the plunger body opening.

2. A metering device according to claim 1, further comprising a locking device with at least one locking element on the metering plunger body and with at least one counter locking element on the storage container for defining at least two metering locking lift positions of the metering plunger body in the storage container, from the starting position, which positions define the corresponding metering position of the metering plunger body and differ in the distance between the starting position and the respective metering position.

3. A metering device according to claim 2, wherein the metering sleeve comprises an inner metering sleeve section, which is guided in a sealed manner in the storage container, and an outer metering sleeve section, which is guided on an outer wall of the storage container, wherein the locking device is arranged in the area of a guide of the outer metering sleeve section on the storage container.

4. A metering device according to claim 1, wherein a seal is formed between the metering plunger body and the storage container by a seal formed in one piece on the metering plunger body.

5. A metering device according to claim 1, wherein the metering sleeve bottom is sealed against the plunger body base by a sealing body, which in the open relative rotational position provides access between the inside of the storage container and the inside of the inner plunger body.

6. A metering device according to claim 5, wherein at least one of the sealing body and the one-way valve is arranged in a recess in the metering sleeve bottom.

7. A metering device according to claim 1, comprising a one-way valve in the passage between the inside of the storage container and the inside of the inner plunger body, which allows the flow of preparation from the storage container into the inner plunger body and blocks the flow of preparation in opposite direction.

8. A metering device according to claim 1, wherein a guide of a rotational movement of the outer metering sleeve to the inner plunger body is formed by at least one partly circular elongated hole arranged in circumferential direction about the longitudinal axis, formed in one of the metering sleeve and the plunger body and a guiding pin running in the elongated hole formed on one of the plunger body and the metering sleeve.

9. A metering device according to claim 1, comprising a stop device with a stop body secured axially on the storage container and a counter stop body secured axially on the metering sleeve for determining a metering lock lift position of the metering plunger body in the storage container, which represents a corresponding metering position of the metering plunger body, starting from an inserted starting position of the metering plunger body in the storage container.

10. A metering device according to claim 9, wherein the metering sleeve has an inner metering sleeve section, which is guided in a sealed manner in the storage container, and an outer metering sleeve section, which is guided on an outer wall of the storage container, wherein the stop body is arranged in the area of a guide of the outer metering sleeve section on the storage container.

11. A metering device according to claim 9, wherein the stop body can be displaced in an elongated hole (of the metering sleeve for determining the metering position.

12. A metering device according to claim 9, wherein the stop body has a locking structure and is displaceable between a release position, in which the locking structure is disengaged, and a locking position, in which the locking structure cooperates with a complementary locking counter structure, which is formed on the storage container, so that in the locking position the stop body is secured axially on the storage container.

13. A metering device according to claim 12, comprising a first locking device, which secures the stop body surmountably in the release position, and a second locking device, which secures the stop body after surmounting the first locking device in the locking position.

14. A metering device according to claim 1, wherein the storage container is in two parts and comprises an inner metering cylinder with a supply volume and an outer guiding sleeve, wherein the metering cylinder and the guiding sleeve are secured axially to one another and, in an axial relative end position, against relative rotation to one another about the longitudinal axis.

15. A metering device according to claim 14, comprising an axial/rotation protection device, which in a first axial position of the metering cylinder to the guiding sleeve allows a relative rotation of the metering cylinder to the guiding sleeve about the longitudinal axis and in a second axial position of the metering cylinder to the guiding sleeve blocks a relative rotation of the metering cylinder to the guiding sleeve about the longitudinal axis, wherein by means of a relative rotation of the metering cylinder to the guiding sleeve in the first axial position a fine definition can be made of an axial position of stop body to the metering cylinder and thereby the metering position of the metering plunger body in the storage container.

16. A metering device for the metered administration of a flowable preparation together with a flowable carrier medium, comprising:
   a storage container for the preparation, which communicates with the environment via at least one access opening,
   a metering plunger body, which is displaceable in a sealed manner at least partially in the storage container between
      a starting position, in which the metering plunger body is pushed fully into the storage container and
      at least one metering position, in which the metering plunger body is pushed out of the storage container by a distance corresponding to a desired metering amount,
   wherein the metering plunger body is hollow and provides a through opening between
      a plunger body opening, which faces the at least one access opening, and
      a suction opening of the metering plunger body accessible from the outside,
   wherein the metering plunger body has an outer metering sleeve and an inner, hollow plunger body, which is rotatable about a longitudinal axis of the metering device in the metering sleeve,
   wherein the metering sleeve in a metering sleeve bottom facing the access opening of the storage container has at least one metering sleeve opening arranged eccentric to the longitudinal axis, wherein the inner plunger body in a plunger body bottom facing the access opening of the storage container comprises a plunger body opening arranged eccentric to the longitudinal axis, wherein in an open relative rotational position of the metering sleeve relative to the inner plunger body a passage is opened between the inside of the storage container and the inside of the inner plunger body through the metering sleeve opening and the plunger body opening, wherein a one-way valve is positioned in the passage between the inside of the storage container and the inside of the inner plunger body, which allows the flow of preparation from the storage container into the inner plunger body and blocks the flow of preparation in opposite direction, and wherein in a closed relative rotational position of the metering sleeve relative to the inner plunger body the passage is closed between the inside of the storage container and the inside of the inner plunger body through the metering sleeve opening and the plunger body opening.

17. A metering device for the metered administration of a flowable preparation together with a flowable carrier medium, comprising:
a storage container for the preparation, which communicates with the environment via at least one access opening,
a metering plunger body, which is displaceable in a sealed manner at least partially in the storage container between
a starting position, in which the metering plunger body is pushed fully into the storage container and
at least one metering position, in which the metering plunger body is pushed out of the storage container by a distance corresponding to a desired metering amount,
wherein the metering plunger body is hollow and provides a through opening between
a plunger body opening, which faces the at least one access opening, and
a suction opening of the metering plunger body accessible from the outside,
wherein the metering plunger body has an outer metering sleeve and an inner, hollow plunger body, which is rotatable about a longitudinal axis of the metering device in the metering sleeve,
wherein the metering sleeve in a metering sleeve bottom facing the access opening of the storage container has at least one metering sleeve opening arranged eccentric to the longitudinal axis,
wherein the inner plunger body in a plunger body bottom facing the access opening of the storage container comprises a plunger body opening arranged eccentric to the longitudinal axis,
wherein in an open relative rotational position of the metering sleeve relative to the inner plunger body a passage is opened between the inside of the storage container and the inside of the inner plunger body through the metering sleeve opening and the plunger body opening,
wherein the metering sleeve bottom is sealed against the plunger body base by a sealing body, which in the open relative rotational position provides access between the inside of the storage container and the inside of the inner plunger body,
wherein at least one of the sealing body and a one-way valve is arranged in a recess in the metering sleeve bottom, and wherein in a closed relative rotational position of the metering sleeve relative to the inner plunger body the passage is closed between the inside of the storage container and the inside of the inner plunger body through the metering sleeve opening and the plunger body opening.

18. A metering device for the metered administration of a flowable preparation together with a flowable carrier medium, comprising:
a storage container for the preparation, which communicates with the environment via at least one access opening,
a metering plunger body, which is displaceable in a sealed manner at least partially in the storage container between
a starting position, in which the metering plunger body is pushed fully into the storage container and
at least one metering position, in which the metering plunger body is pushed out of the storage container by a distance corresponding to a desired metering amount,
wherein the metering plunger body is hollow and provides a through opening between
a plunger body opening, which faces the at least one access opening, and
a suction opening of the metering plunger body accessible from the outside,
wherein the metering plunger body has an outer metering sleeve and an inner, hollow plunger body, which is rotatable about a longitudinal axis of the metering device in the metering sleeve,
wherein a guide of a rotational movement of the outer metering sleeve to the inner plunger body is formed by at least one partly circular elongated hole arranged in circumferential direction about the longitudinal axis, formed in one of the metering sleeve and the plunger body and a guiding pin running in the elongated hole formed on one of the plunger body and the metering sleeve,
wherein the metering sleeve in a metering sleeve bottom facing the access opening of the storage container has at least one metering sleeve opening arranged eccentric to the longitudinal axis,
wherein the inner plunger body in a plunger body bottom facing the access opening of the storage container comprises a plunger body opening arranged eccentric to the longitudinal axis,
wherein in an open relative rotational position of the metering sleeve relative to the inner plunger body a passage is opened between the inside of the storage container and the inside of the inner plunger body through the metering sleeve opening and the plunger body opening, and
wherein in a closed relative rotational position of the metering sleeve relative to the inner plunger body the passage is closed between the inside of the storage container and the inside of the inner plunger body through the metering sleeve opening and the plunger body opening.

19. A metering device for the metered administration of a flowable preparation together with a flowable carrier medium, comprising:
a storage container for the preparation, which communicates with the environment via at least one access opening,
a metering plunger body, which is displaceable in a sealed manner at least partially in the storage container between
a starting position, in which the metering plunger body is pushed fully into the storage container and at least one metering position, in which the metering plunger body is pushed out of the storage container by a distance corresponding to a desired metering amount, wherein the metering plunger body is hollow and provides a through opening between
  a plunger body opening, which faces the at least one access opening, and
  a suction opening of the metering plunger body accessible from the outside, wherein the metering plunger body has an outer metering sleeve and an inner, hollow plunger body, which is rotatable about a longitudinal axis of the metering device in the metering sleeve, wherein the metering sleeve in a metering sleeve bottom facing the access opening of the storage container has at least one metering sleeve opening arranged eccentric to the longitudinal axis, wherein the inner plunger body in a plunger body bottom facing the access opening of the storage container comprises a plunger body opening arranged eccentric to the longitudinal axis, wherein in an open relative rotational position of the metering sleeve relative to the inner plunger body a passage is opened between the inside of the storage container and the inside of the inner plunger body through the metering sleeve opening and the plunger body opening, wherein in a closed relative rotational position of the metering sleeve relative to the inner plunger body the passage is closed between the inside of the storage container and the inside of the inner plunger body through the metering sleeve opening and the plunger body opening, wherein the metering device further comprises a stop device with a stop body secured axially on the storage container and a counter stop body secured axially on the metering sleeve for determining a metering lock lift position of the metering plunger body in the storage container, which represents a corresponding metering position of the metering plunger body, starting from an inserted starting position of the metering plunger body in the storage container, and wherein the metering sleeve has an inner metering sleeve section, which is guided in a sealed manner in the storage container, and an outer metering sleeve section, which is guided on an outer wall of the storage container, wherein the stop body is arranged in the area of a guide of the outer metering sleeve section on the storage container.

20. A metering device for the metered administration of a flowable preparation together with a flowable carrier medium, comprising:
  a storage container for the preparation, which communicates with the environment via at least one access opening,
  a metering plunger body, which is displaceable in a sealed manner at least partially in the storage container between
    a starting position, in which the metering plunger body is pushed fully into the storage container and
    at least one metering position, in which the metering plunger body is pushed out of the storage container by a distance corresponding to a desired metering amount,
  wherein the metering plunger body is hollow and provides a through opening between
    a plunger body opening, which faces the at least one access opening, and
    a suction opening of the metering plunger body accessible from the outside,
  wherein the metering plunger body has an outer metering sleeve and an inner, hollow plunger body, which is rotatable about a longitudinal axis of the metering device in the metering sleeve,
  wherein the metering sleeve in a metering sleeve bottom facing the access opening of the storage container has at least one metering sleeve opening arranged eccentric to the longitudinal axis,
  wherein the inner plunger body in a plunger body bottom facing the access opening of the storage container comprises a plunger body opening arranged eccentric to the longitudinal axis,
  wherein in an open relative rotational position of the metering sleeve relative to the inner plunger body a passage is opened between the inside of the storage container and the inside of the inner plunger body through the metering sleeve opening and the plunger body opening,
  wherein in a closed relative rotational position of the metering sleeve relative to the inner plunger body the passage is closed between the inside of the storage container and the inside of the inner plunger body through the metering sleeve opening and the plunger body opening,
  wherein the metering device further comprises a stop device with a stop body secured axially on the storage container and a counter stop body secured axially on the metering sleeve for determining a metering lock lift position of the metering plunger body in the storage container, which represents a corresponding metering position of the metering plunger body, starting from an inserted starting position of the metering plunger body in the storage container,
  wherein the stop body has a locking structure and is displaceable between a release position, in which the locking structure is disengaged, and a locking position, in which the locking structure cooperates with a complementary locking counter structure, which is formed on the storage container, so that in the locking position the stop body is secured axially on the storage container, and
  wherein the metering device further comprises a first locking device, which secures the stop body surmountably in the release position, and a second locking device, which secures the stop body after surmounting the first locking device in the locking position.

21. A metering device for the metered administration of a flowable preparation together with a flowable carrier medium, comprising:
  a storage container for the preparation, which communicates with the environment via at least one access opening,
  a metering plunger body, which is displaceable in a sealed manner at least partially in the storage container between
    a starting position, in which the metering plunger body is pushed fully into the storage container and
    at least one metering position, in which the metering plunger body is pushed out of the storage container by a distance corresponding to a desired metering amount,
  wherein the metering plunger body is hollow and provides a through opening between
    a plunger body opening, which faces the at least one access opening, and
    a suction opening of the metering plunger body accessible from the outside, wherein the metering plunger body has an outer metering sleeve and an inner, hollow plunger body, which is rotatable about a longitudinal axis of the metering device in the metering sleeve, wherein the metering sleeve in a metering sleeve bottom facing the access opening of the storage container has at least one metering sleeve opening arranged eccentric to the longitudinal axis, wherein the inner plunger body in a plunger body bottom facing the access opening of the storage container comprises a plunger body opening arranged eccentric to the longitudinal axis, wherein in an open relative rotational position of the metering sleeve relative to the inner plunger body a passage is opened between the inside of the storage container and the inside of the inner plunger body through the metering sleeve opening and the plunger body opening, wherein in a closed relative rotational position of the metering sleeve relative to the inner plunger body the passage is closed between the inside of the storage container and the inside of the inner plunger body through the metering sleeve opening and the plunger body opening, wherein the storage container is in two parts and comprises an inner metering cylinder with a supply volume and an outer guiding sleeve, wherein the metering cylinder and the guiding sleeve are secured axially to one another and, in an axial relative end position, against relative rotation to one another about the longitudinal axis, and wherein the metering device further comprises an axial/rotation protection device, which in a first axial position of the metering cylinder to the guiding sleeve allows a relative rotation of the metering cylinder to the guiding sleeve about the longitudinal axis and in a second axial position of the metering cylinder to the guiding sleeve blocks a relative rotation of the metering cylinder to the guiding sleeve about the longitudinal axis, wherein by means of a relative rotation of the metering cylinder to the guiding sleeve in the first axial position, the axial position of a stop body can be finely adjusted relative to the metering cylinder to thereby adjust the metering position of the metering plunger body in the storage container.

* * * * *